(12) United States Patent
Wright et al.

(10) Patent No.: US 10,925,776 B2
(45) Date of Patent: Feb. 23, 2021

(54) DISPOSABLE FLOATING ABSORBENT CORE AND DISPOSABLE ABSORBENT ASSEMBLY INCLUDING SAME, AND METHOD OF MAKING SAME

(71) Applicants: Andrew Wright, Derbyshire (GB); Eugenio Varona, Marietta, GA (US); Dennis Smid, Wolvega (NL)

(72) Inventors: Andrew Wright, Derbyshire (GB); Eugenio Varona, Marietta, GA (US); Dennis Smid, Wolvega (NL)

(73) Assignee: DSG Technology Holdings Ltd., Kwai Chung (HK)

( * ) Notice: Subject to any disclaimer, the term of this patent is extended or adjusted under 35 U.S.C. 154(b) by 367 days.

(21) Appl. No.: 15/853,701

(22) Filed: Dec. 22, 2017

(65) Prior Publication Data

US 2018/0185204 A1 Jul. 5, 2018

Related U.S. Application Data

(60) Provisional application No. 62/438,253, filed on Dec. 22, 2016.

(51) Int. Cl.
*A61F 13/15* (2006.01)
*A61F 13/49* (2006.01)
*A61F 13/511* (2006.01)

(52) U.S. Cl.
CPC .... *A61F 13/49061* (2013.01); *A61F 13/4902* (2013.01); *A61F 13/4906* (2013.01);
(Continued)

(58) Field of Classification Search
CPC .......... A61F 13/49061; A61F 13/49011; A61F 13/49012; A61F 13/49017; A61F 13/4902;
(Continued)

(56) References Cited

U.S. PATENT DOCUMENTS

| 4,525,229 A | 6/1985 | Suzuki et al. |
| 5,147,487 A | 9/1992 | Nomura et al. |

(Continued)

FOREIGN PATENT DOCUMENTS

| EP | 0623331 A2 | 11/1994 |
| EP | 0962207 A2 | 12/1999 |

(Continued)

OTHER PUBLICATIONS

Notification of Transmittal of International Search Report and Written Opinion dated Mar. 29, 2018 (issued in PCT Application No. PCT/US2017/068364) [10 pages].

(Continued)

*Primary Examiner* — Jacqueline F Stephens
(74) *Attorney, Agent, or Firm* — Alberto Q. Amatong, Jr.; Amatong McCoy LLC

(57) ABSTRACT

An absorbent article is disclosed. The absorbent article includes a core and a chassis. One or more discrete bonding zones bond the core to the chassis, and one or more unbonded zones of the core are not bonded to the chassis, forming a floating core. The core is not elastically coupled with the chassis. A method of making the absorbent article may include selectively bonding the chassis to the core at discrete bonding zones.

21 Claims, 22 Drawing Sheets

(52) U.S. Cl.
CPC .. *A61F 13/49011* (2013.01); *A61F 13/49012* (2013.01); *A61F 13/49017* (2013.01); *A61F 2013/49022* (2013.01); *A61F 2013/49034* (2013.01); *A61F 2013/49074* (2013.01); *A61F 2013/51182* (2013.01)

(58) Field of Classification Search
CPC ........ A61F 13/4906; A61F 2013/49022; A61F 2013/49034; A61F 2013/49074; A61F 2013/51182
USPC .......... 604/374, 375, 378, 379, 380, 385.01, 604/385.101, 385.31
See application file for complete search history.

(56) References Cited

U.S. PATENT DOCUMENTS

| | | | |
|---|---|---|---|
| 5,360,422 | A | 11/1994 | Brownlee et al. |
| 5,576,091 | A | 11/1996 | Zajaczkowski et al. |
| 5,613,959 | A | 3/1997 | Roessler et al. |
| 6,423,042 | B1 * | 7/2002 | Sasaki ............... A61F 13/49017 604/358 |
| 6,491,676 | B1 | 12/2002 | Suzuki et al. |
| 6,638,262 | B2 | 10/2003 | Suzuki et al. |
| 6,790,798 | B1 | 9/2004 | Suzuki et al. |
| 6,794,557 | B1 | 9/2004 | Klemp et al. |
| 6,869,424 | B1 | 3/2005 | Morman et al. |
| 7,361,246 | B2 | 4/2008 | Chang et al. |
| 7,462,172 | B2 | 12/2008 | Wright et al. |
| 8,083,724 | B2 | 12/2011 | Bittner et al. |
| 8,148,598 | B2 | 4/2012 | Tsang et al. |
| 8,157,781 | B2 | 4/2012 | Takino et al. |
| 8,568,380 | B2 | 10/2013 | Brownlee |
| 8,785,715 | B2 | 7/2014 | Wright et al. |
| 9,205,003 | B2 | 12/2015 | Tsang et al. |
| 2003/0045855 | A1 | 3/2003 | Ono et al. |
| 2005/0288646 | A1 | 12/2005 | LaVon |
| 2009/0320993 | A1 | 12/2009 | Yamamoto |
| 2010/0078119 | A1 | 4/2010 | Yamamoto |
| 2010/0179500 | A1 | 7/2010 | Roe et al. |
| 2011/0130736 | A1 | 6/2011 | Tsang et al. |
| 2012/0071852 | A1 | 3/2012 | Tsang et al. |
| 2014/0276508 | A1 | 9/2014 | Wright et al. |
| 2014/0303582 | A1 | 10/2014 | Wright et al. |
| 2015/0050462 | A1 | 2/2015 | Schroer |
| 2015/0245959 | A1 | 9/2015 | Nelson et al. |
| 2016/0058624 | A1 | 3/2016 | Hohm et al. |
| 2016/0278999 | A1 | 9/2016 | Wang et al. |

FOREIGN PATENT DOCUMENTS

| | | |
|---|---|---|
| EP | 2589359 A1 | 5/2013 |
| WO | 2010109883 A1 | 9/2010 |
| WO | 2012036750 A2 | 3/2012 |
| WO | 2012170341 A1 | 12/2012 |

OTHER PUBLICATIONS

International Preliminary Report on Patentability issued in PCT Application No. PCT/US2017/068364, dated Jul. 4, 2019; 9 pages.
Supplementary EP Search Report, issued in EP Application No. 17884096.3 dated Jul. 17, 2020 [7 pages].

* cited by examiner

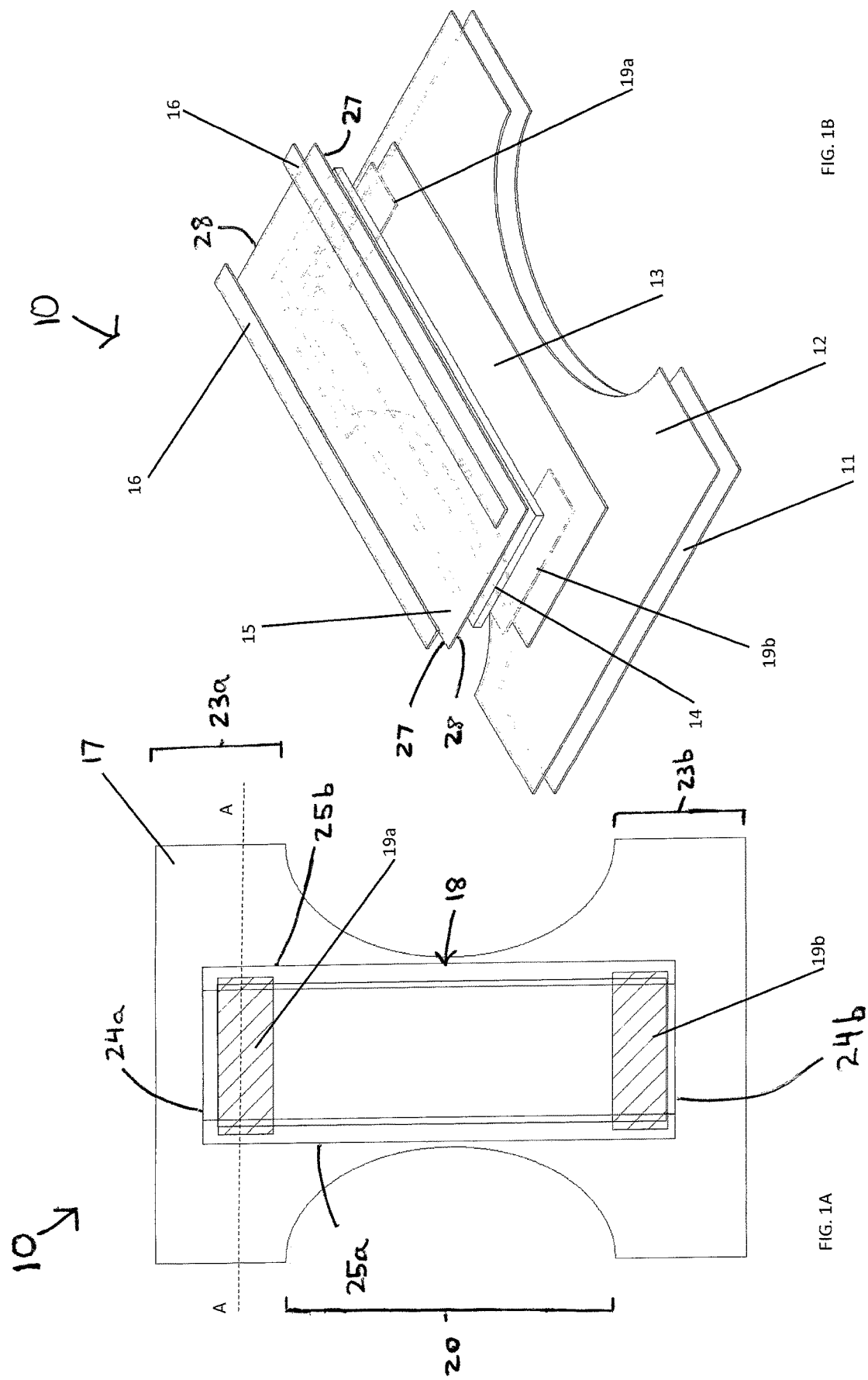

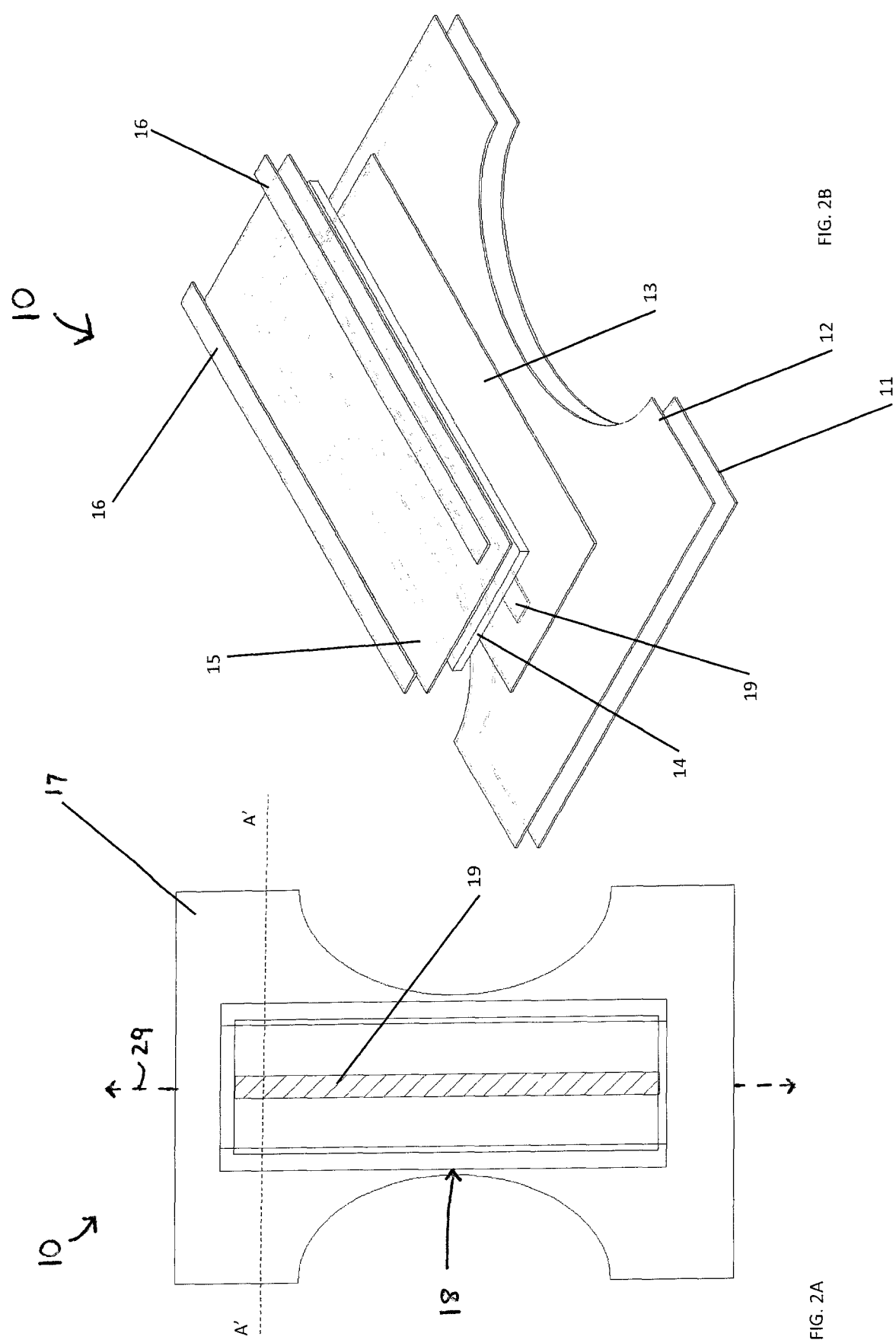

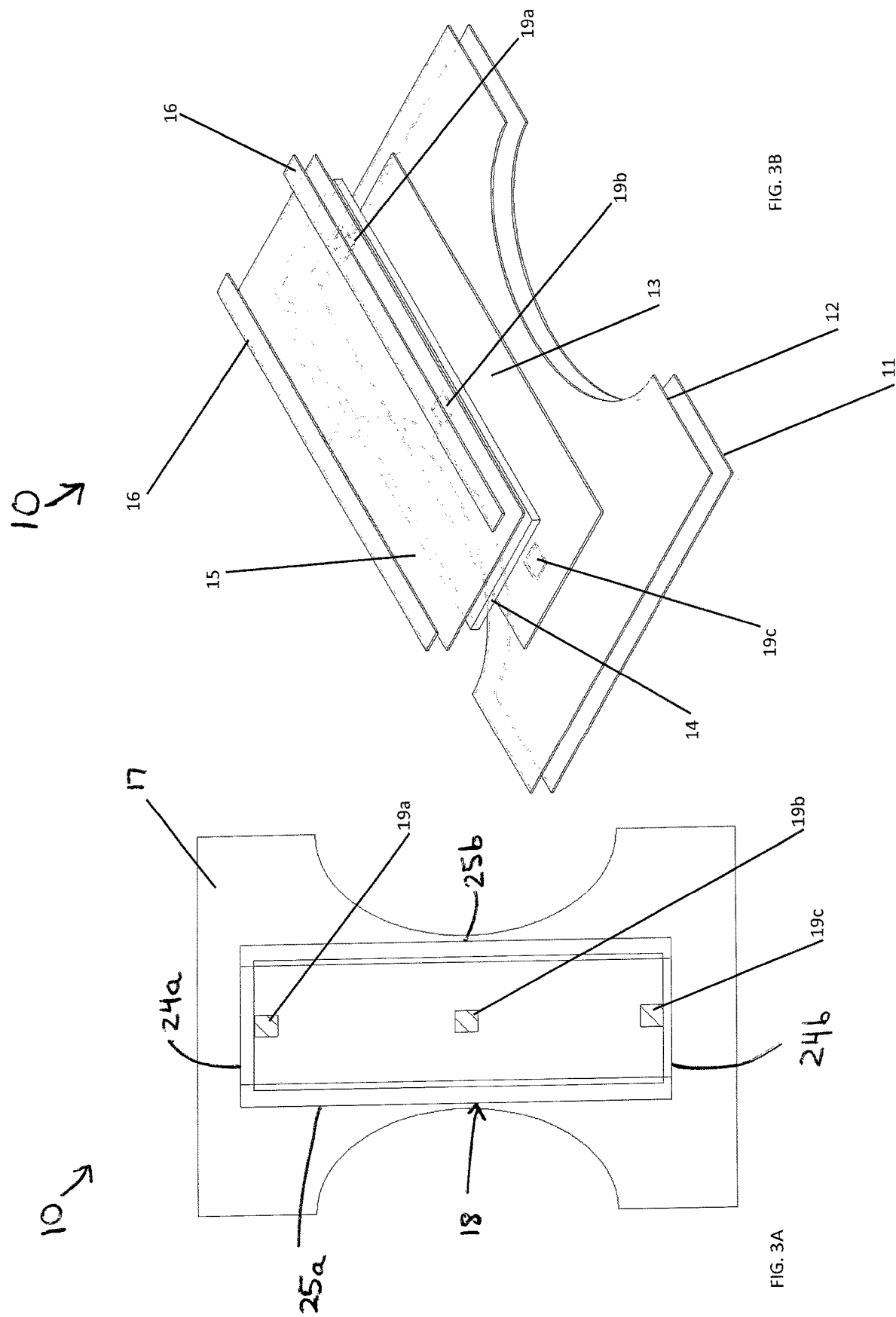

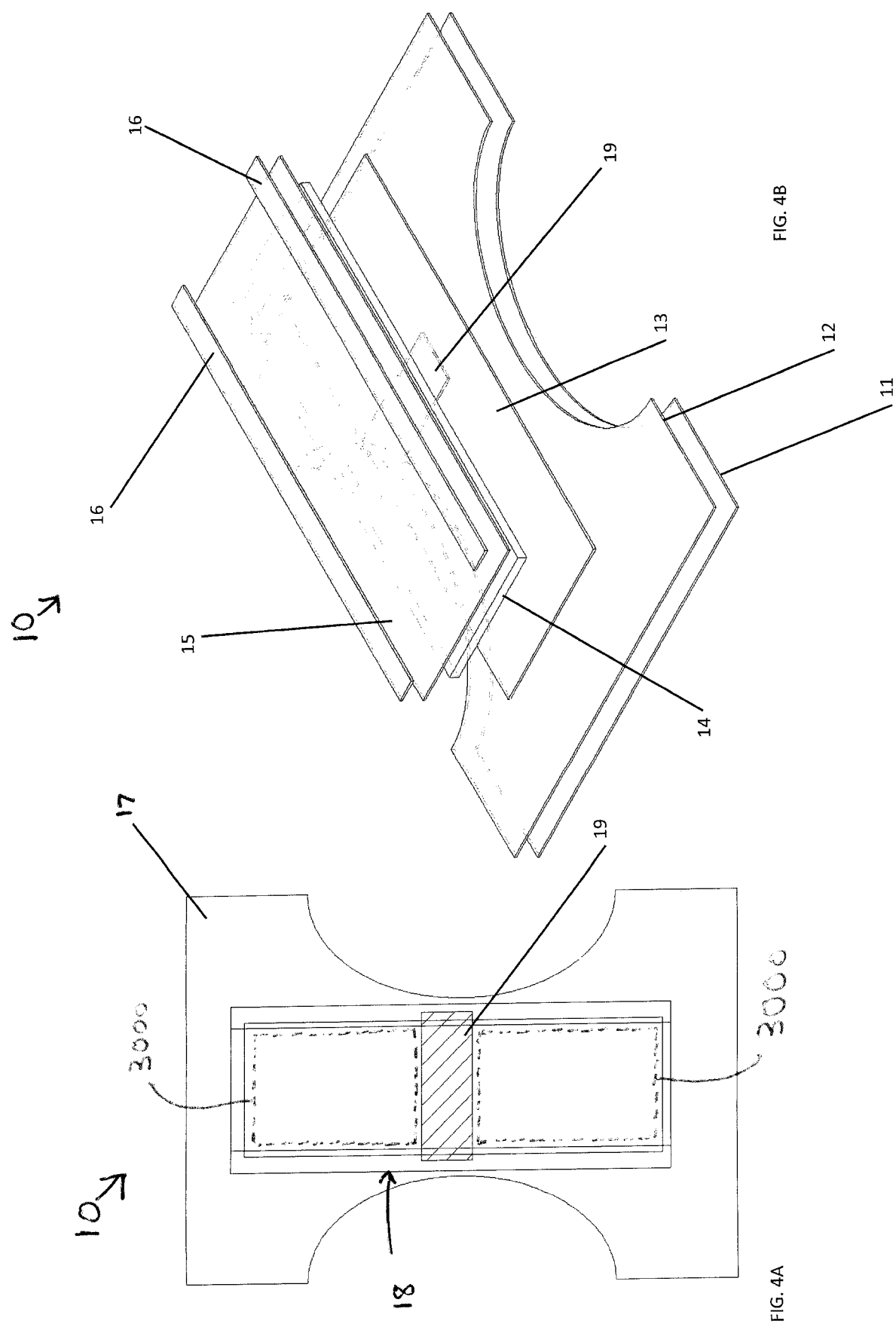

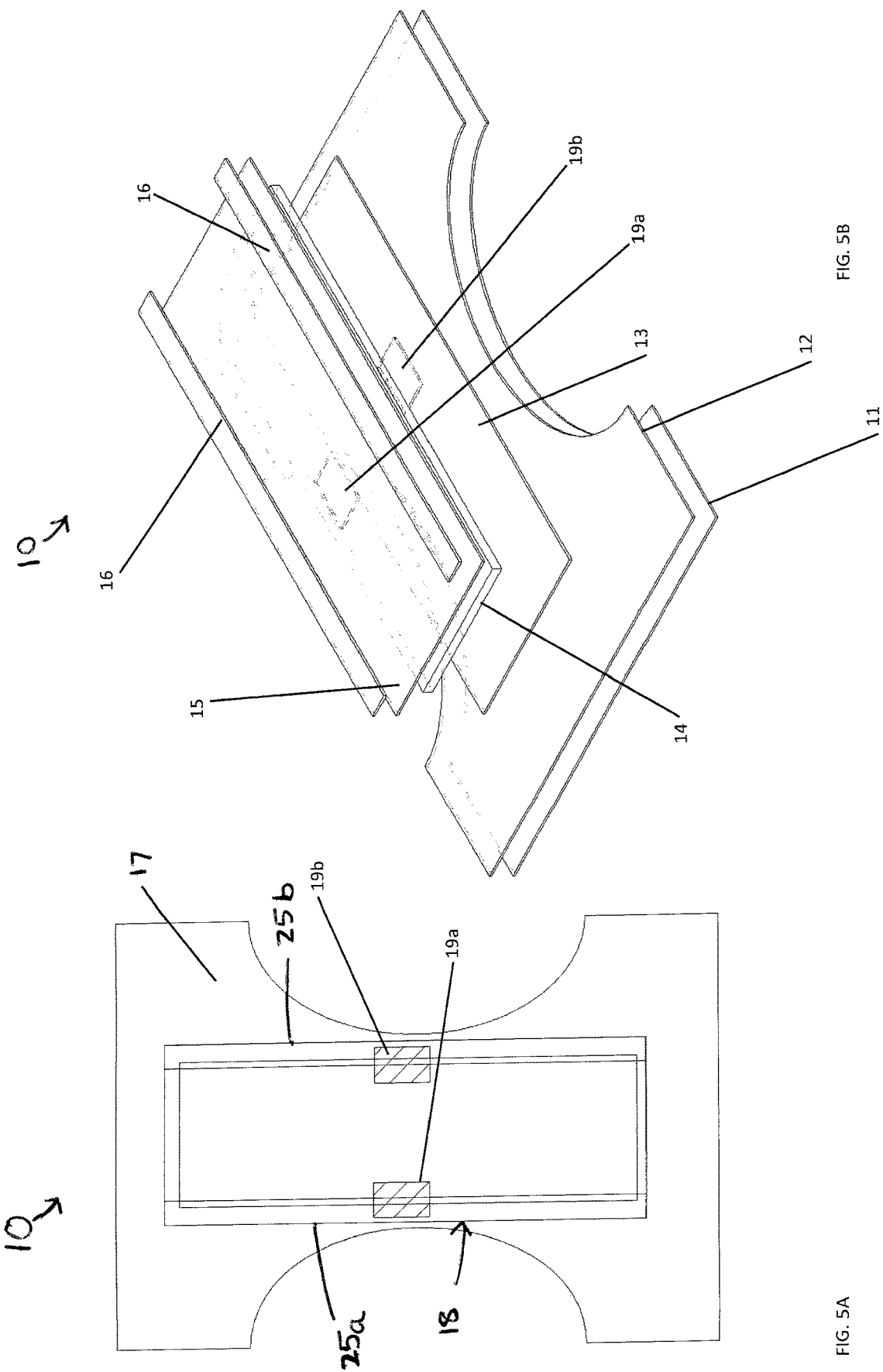

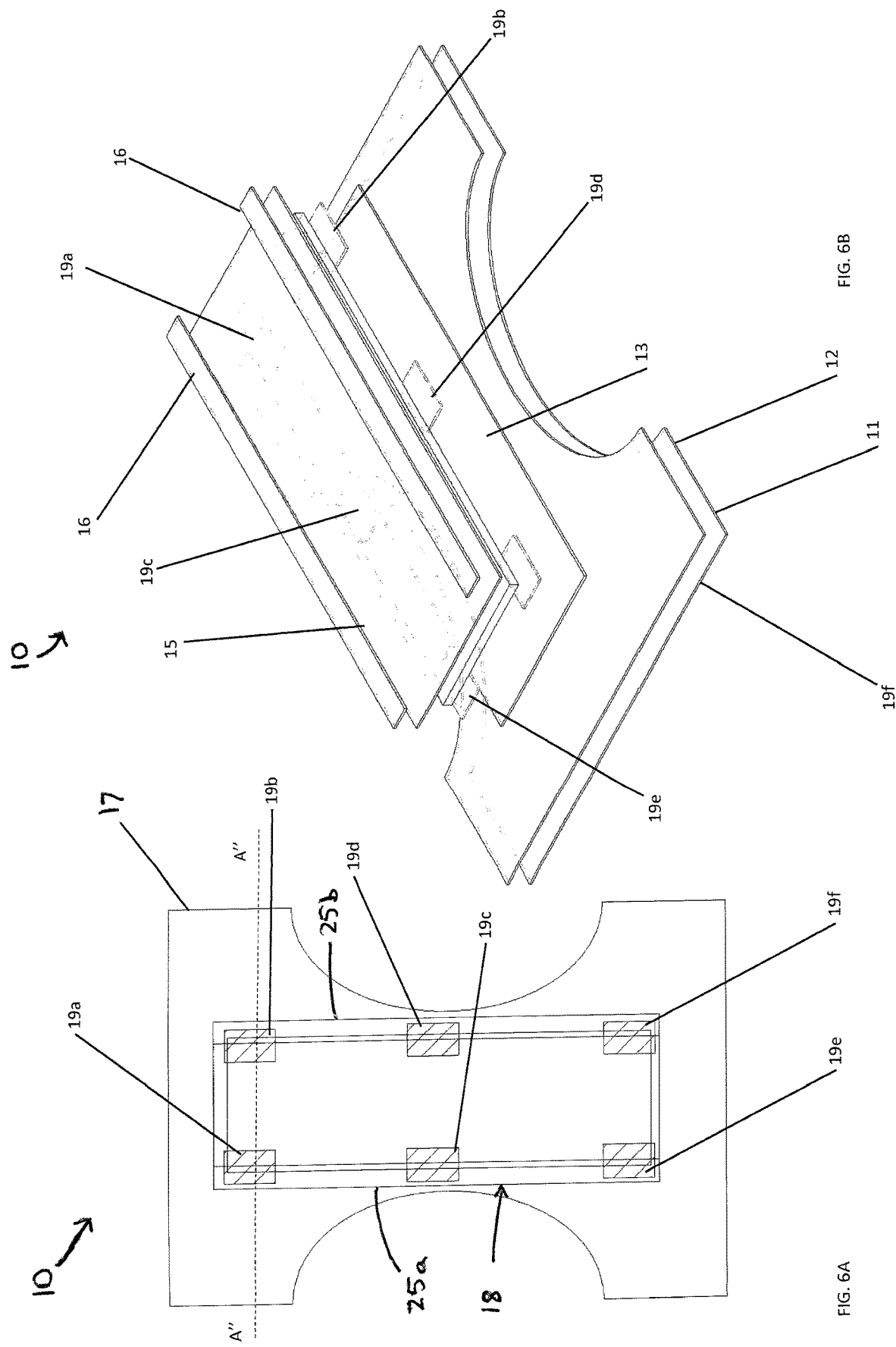

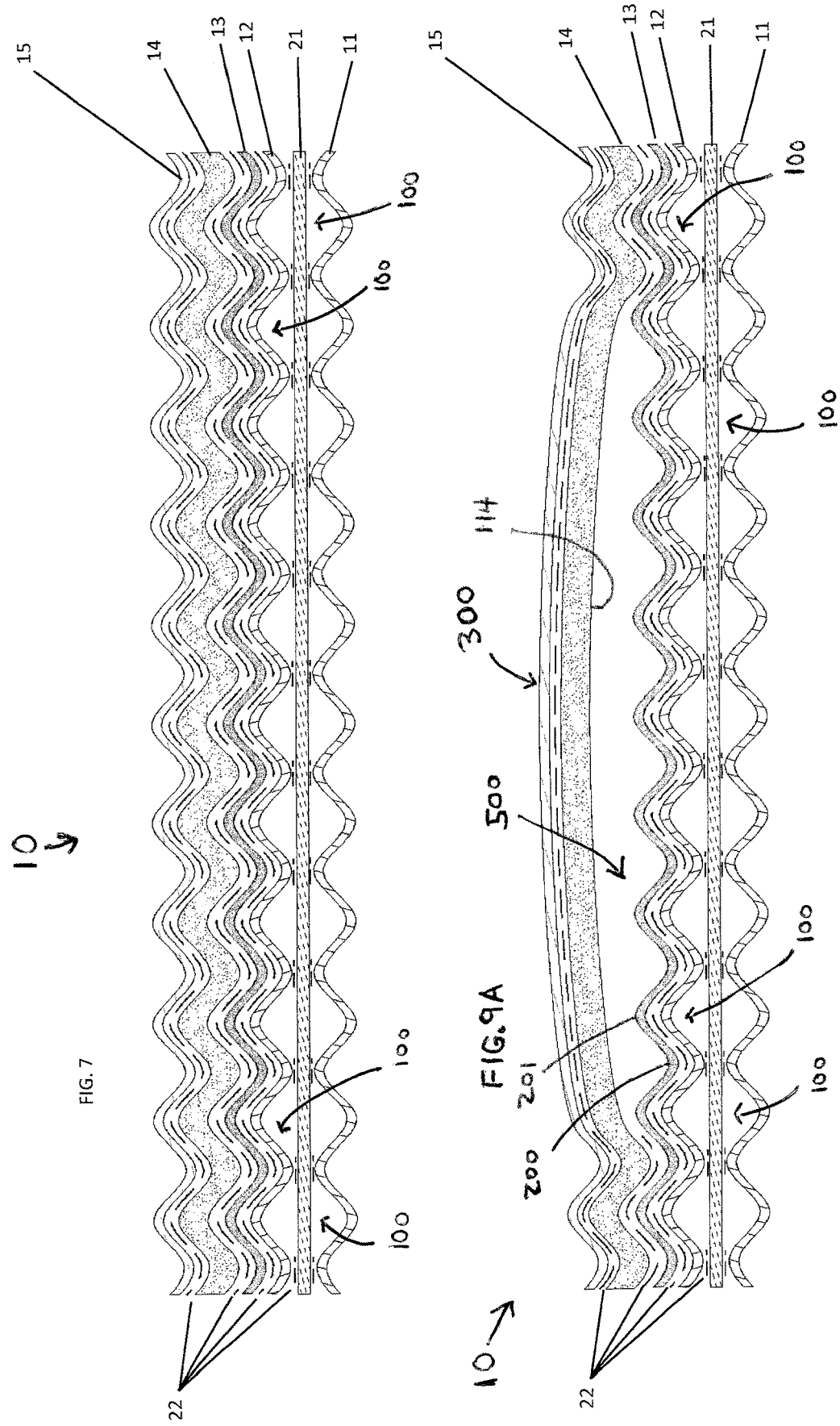

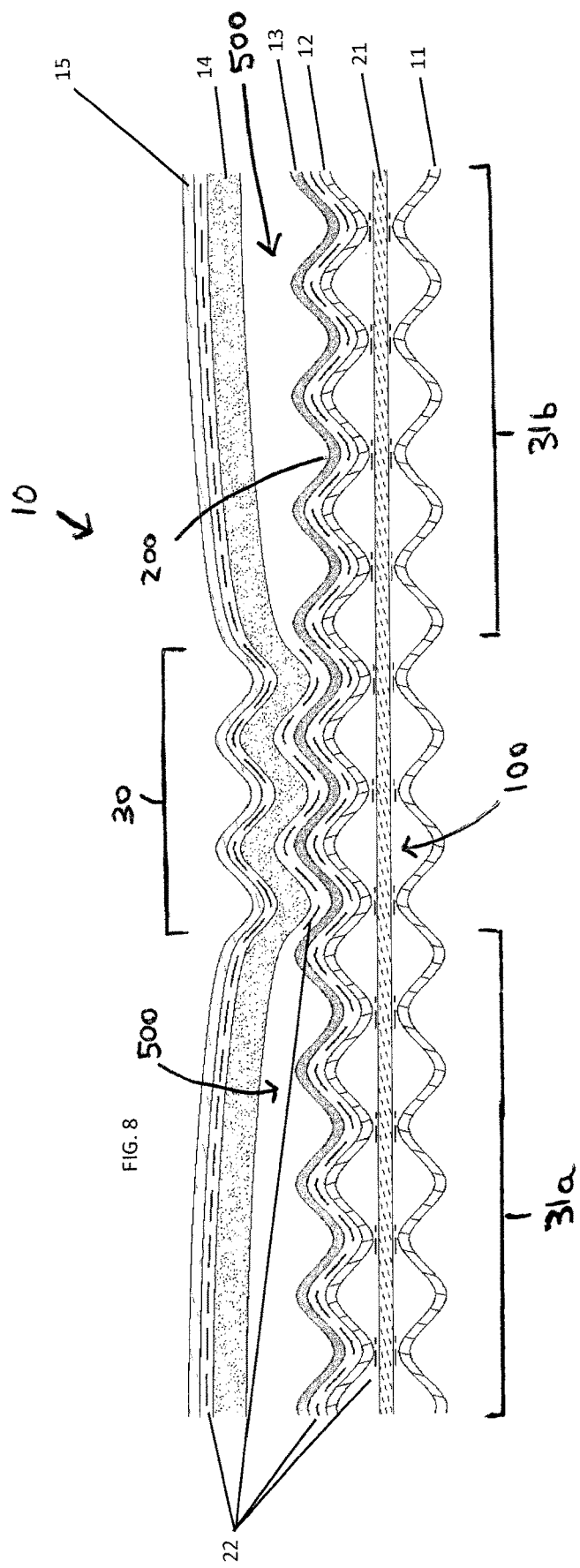

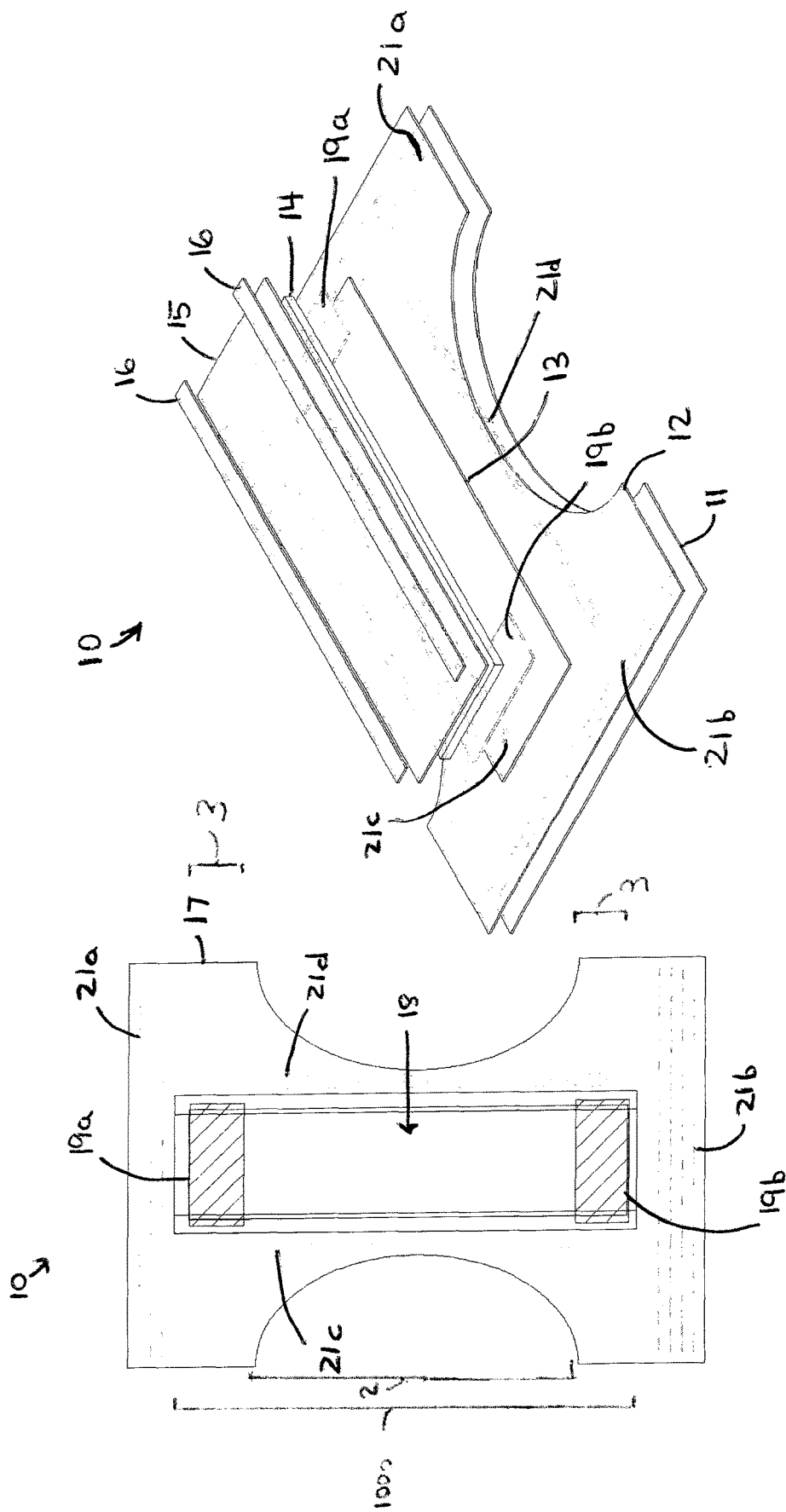

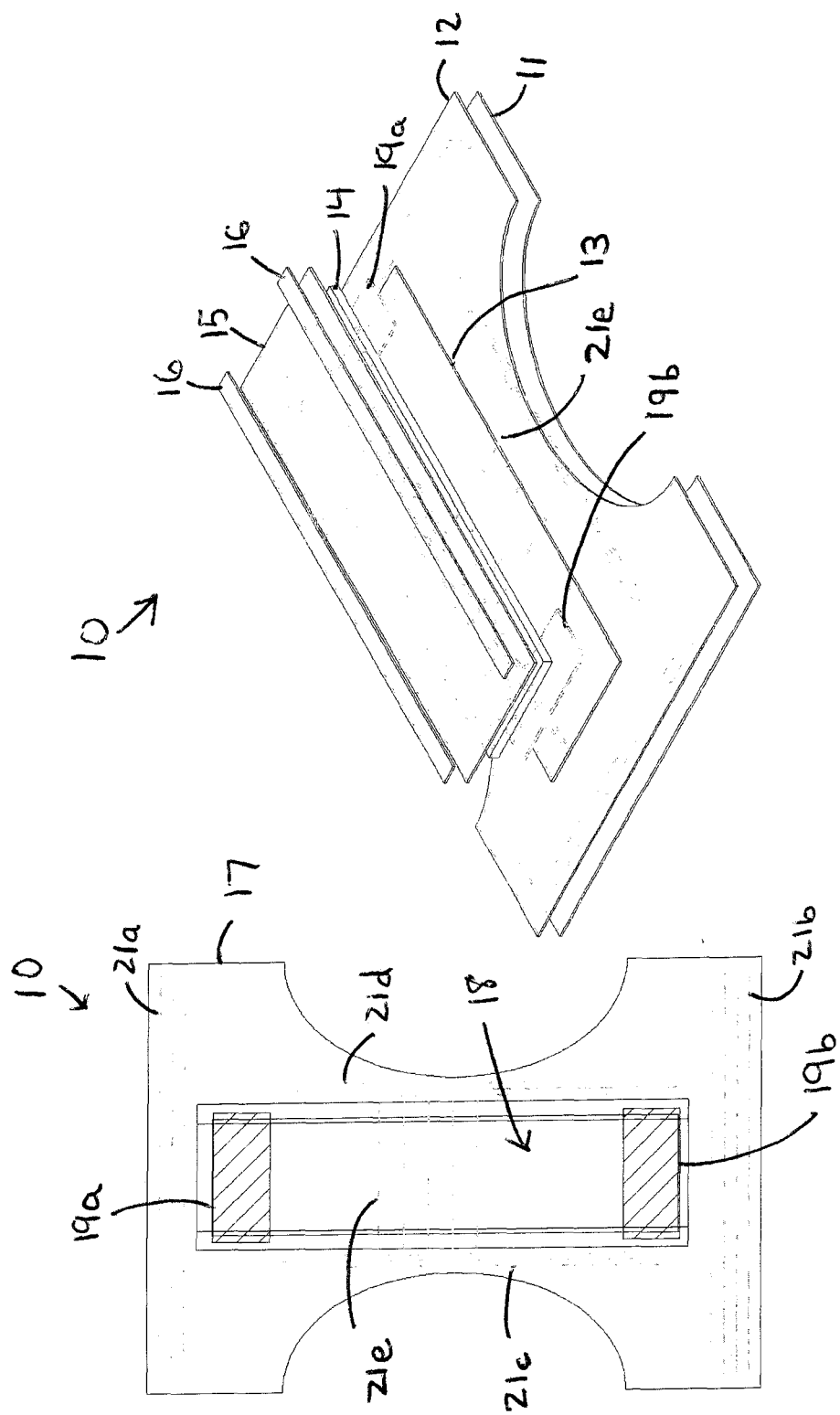

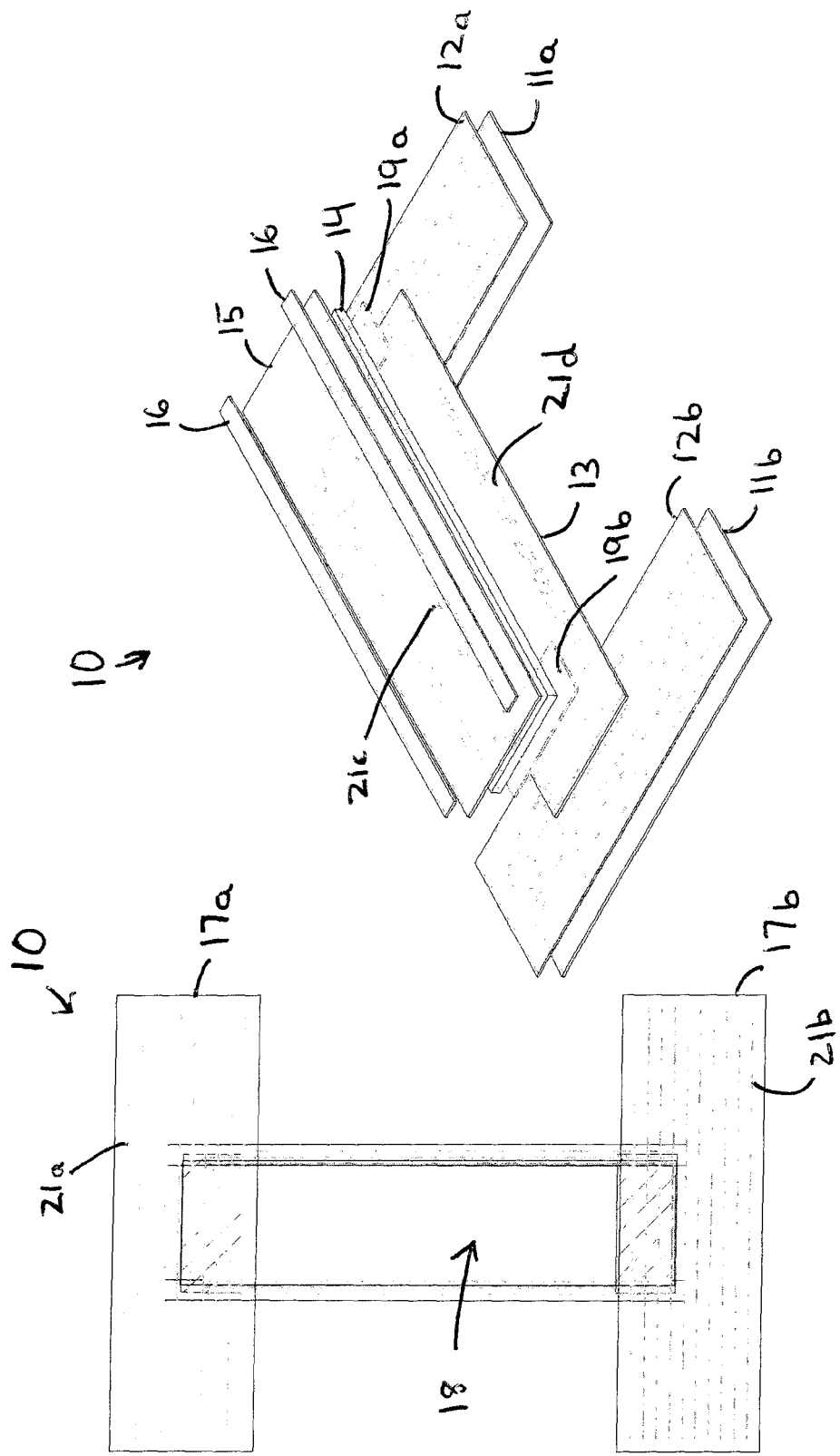

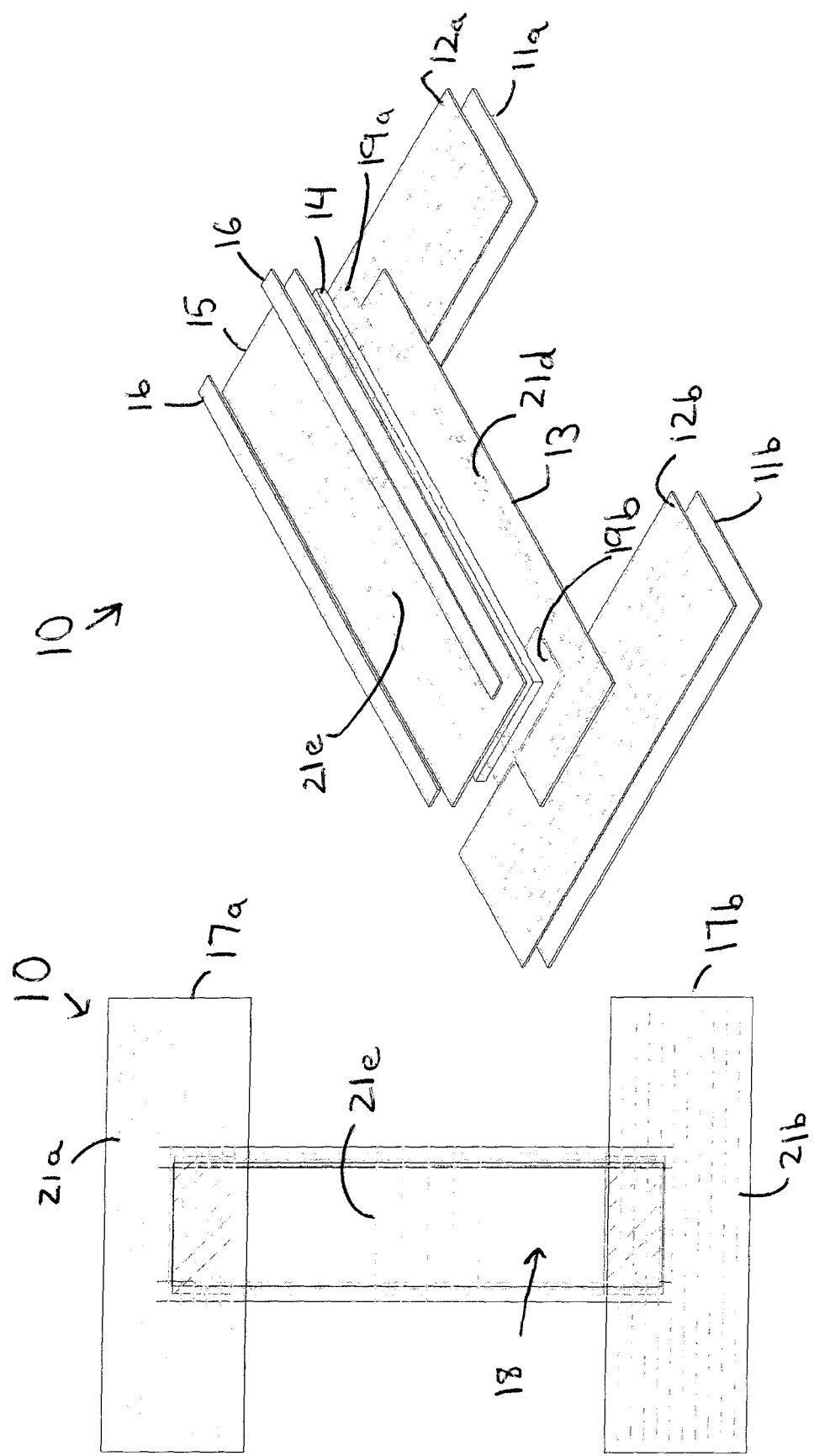

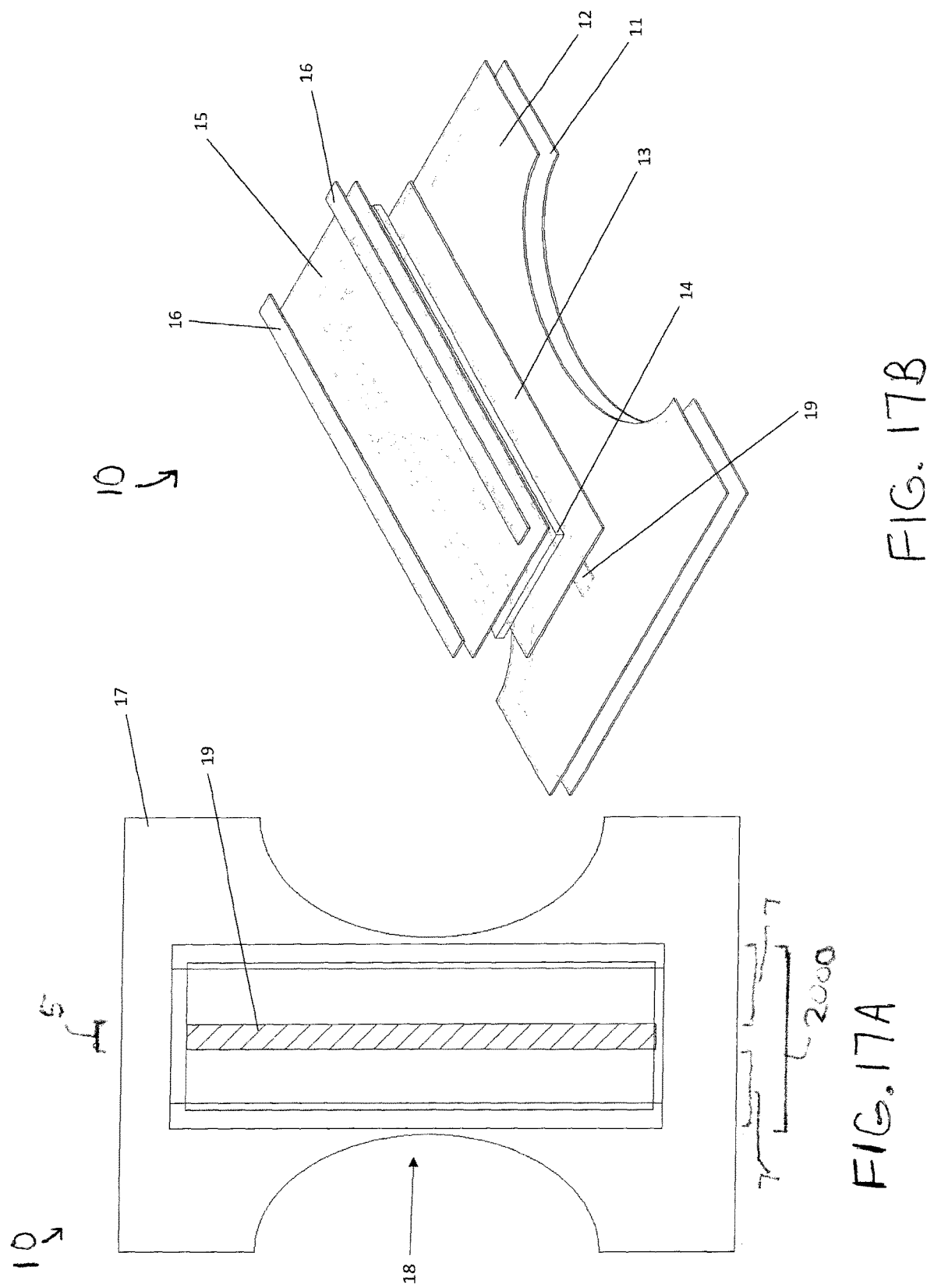

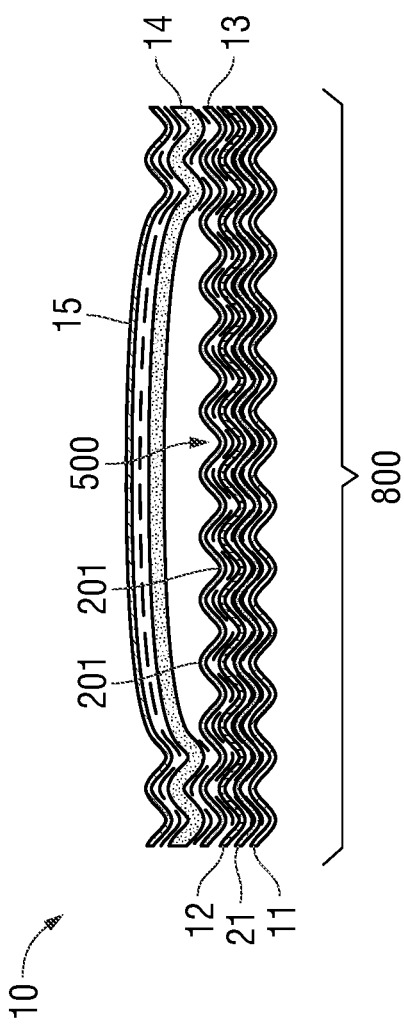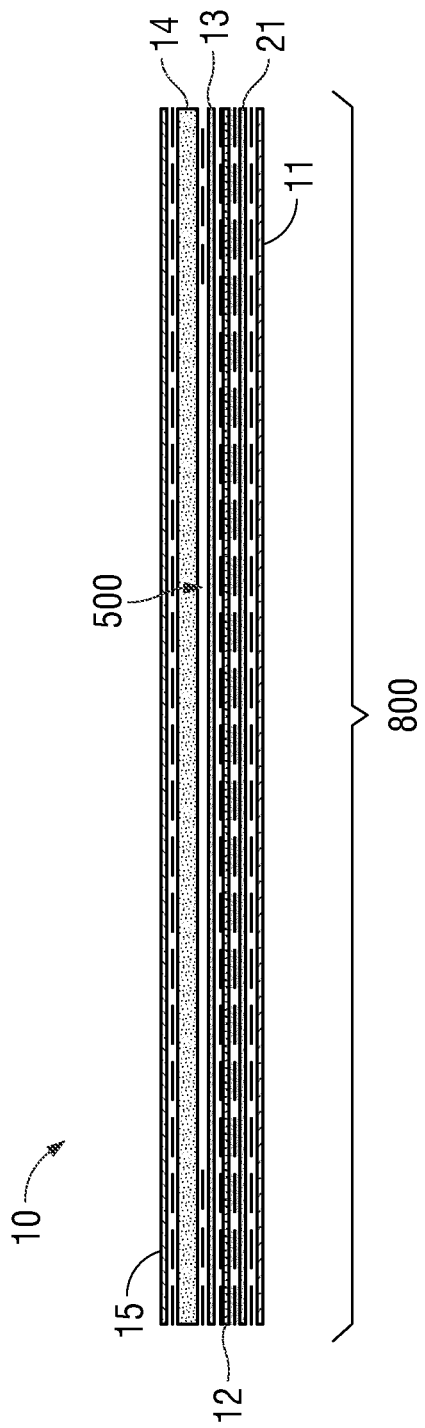
FIG. 20A
FIG. 20B

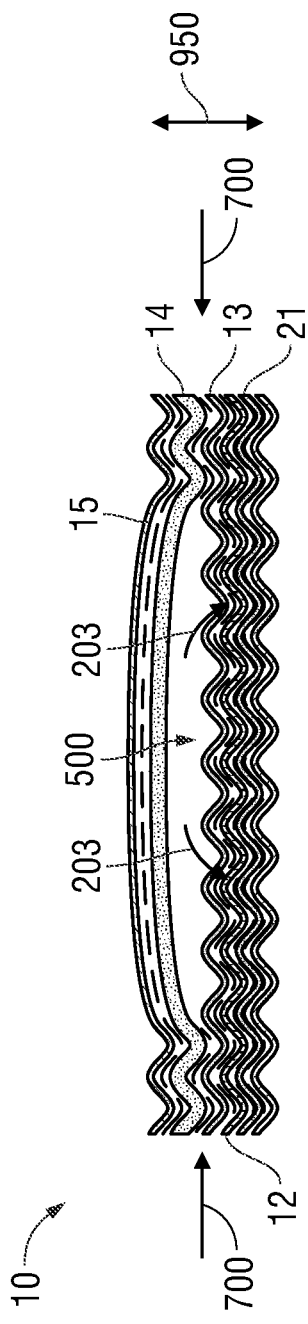
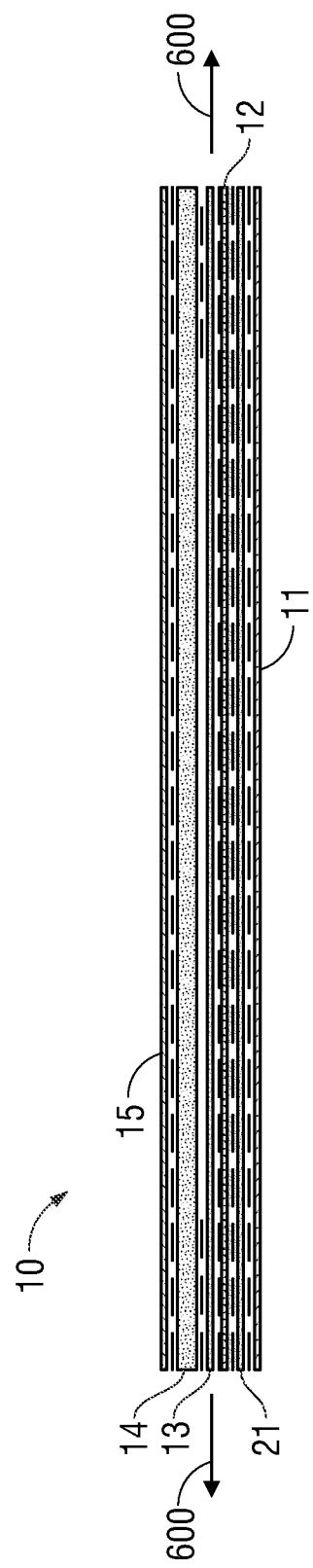
FIG. 21A
FIG. 21B

DISPOSABLE FLOATING ABSORBENT CORE AND DISPOSABLE ABSORBENT ASSEMBLY INCLUDING SAME, AND METHOD OF MAKING SAME

CROSS-REFERENCE TO RELATED APPLICATIONS

The present application claims priority to U.S. Provisional Patent Application No. 62/438,253, filed on Dec. 22, 2016, the entirety of which is incorporated herein by reference for all purposes and made a part of the present disclosure.

FIELD

The present disclosure relates to disposable absorbent articles that include an elasticated chassis and an absorbent core, as well as to method of making the same.

BACKGROUND

When elastic members incorporated into the chassis of an article (e.g., a diaper or the like) is subjected to stretching or contraction, such elastic forces may be transferred to the absorbent core of the article, which may cause discomfort to the user thereof. Reducing or eliminating the transference of such elastic forces from the chassis to the absorbent core may thus increase user comfort.

BRIEF SUMMARY

An embodiment of the present disclosure relates to an absorbent article. The absorbent article includes a core and a chassis. One or more discrete zones that secure or bond the core to the chassis. One or more unbonded zones of the core are not bonded to the chassis. The zones may be part of, or placed on, the core.

Another embodiment of the present disclosure relates to an absorbent article that includes a chassis and a floating core.

Another embodiment of the present disclosure relates to an absorbent article including a chassis and a core, where the core is not elastically coupled with the chassis.

Another embodiment of the present disclosure relates to a method of making an absorbent article. The method includes selectively bonding a chassis to a core at discrete bonding zones.

Another embodiment of the present disclosure relates to an absorbent article including an absorbent core, an elasticated chassis, and a dynamic void space formed therebetween, as well as to methods of making the same.

Certain aspects of the present disclosure provide for an absorbent article that includes an absorbent core composite and an elasticated chassis. The absorbent core composite is also referred to herein as an absorbent core, a core, a floating core, a floating absorbent core, or a core composite. The absorbent core composite may include not only the core absorbent material, but may also include additional layers or materials bonded therewith or secured uniformly thereto, such as an impermeable layer. As used herein "elasticated chassis" refers to a chassis of the absorbent article having elastics incorporated therein (e.g., adhered or otherwise attached thereto), laterally and/or longitudinally, in the waist and/or crotch region of the chassis, such as between two adjacent layers of the chassis. The core is bonded to the chassis via at least one discrete bonding zone that bonds the core with the chassis. The core includes at least one unbonded zone that is unbonded with the chassis. Preferably from 5% to 40% of the surface area of a bottom surface of the core is bonded with the chassis, and from 60% to 95% of the surface area of the bottom surface of the core is unbonded with the chassis. The chassis imparts elasticity to the core at the bonded zones. In some aspects, the perimeter of the core is secured with the chassis and is not included in the unbonded free area thereof.

In some aspects, the unbonded surface area of the core is unrestrained by the chassis and is movable relative to the chassis, such that the core may move vertically relative to the chassis, and the chassis may move without moving the unbonded zones of the core.

In some aspects, the unbonded surface area of the core includes a uniformly unbonded area of the bottom surface of the core. As used herein a "comprehensively unbonded area" refers to a continuous portion of surface area of the bottom surface of the core that is free of bonding to the elasticated chassis (e.g., the free area shown in FIG. 4A). That is, the entire surface area may be moved without impedance from the elasticated chassis.

In some aspects, the unbonded surface area of the core has an unbonded free width that ranges from 50% to 95% of the total width of the core for a core length preferably greater than 50% of the total length of the core. In certain aspects, the unbonded surface area of the core has an unbonded free area that is equal to greater than 50% of the total surface area of the bottom surface of the core.

In some aspects, the unbonded surface area of the core has an unbonded free width that ranges up to 80% or 85% of the width of the core for a core length up to 60% of the total length of the core.

In some aspects, the unbonded surface area of the core has an unbonded free width that ranges from 65% to 85% of the width of the core for a core length up to 70% of the total length of the core.

In some aspects, the unbonded surface area of the core has an unbonded free width that ranges from 50% to 95% of the total width of the core for a core length up to 80% of the total length of the core.

In some aspects, the unbonded surface area of the core has an unbonded free width that ranges from 50% to 95% of the total width of the core for a core length up to 90% of the total length of the core.

In some aspects, the unbonded surface area of the core has an unbonded free width that ranges from 50% to 95% of the total width of the core for a core length up to 95% of the total length of the core. Where numerical ranges or limitations are expressly stated, such express ranges or limitations should be understood to include iterative ranges or limitations of like magnitude falling within the expressly stated ranges or limitations (e.g., from 50 to 95 includes from 55 to 90, 66, greater than 70, etc.).

In certain aspects, when elastics of the chassis are in a contracted state, a void space is positioned between the absorbent core and the elasticated chassis. The void space is coincident with the unbonded zones of the absorbent core.

Some aspects of the present disclosure provide for an absorbent article that includes an absorbent core and an elasticated chassis imparting elasticity to the core at one or more bonding zones. A void space is formed between the elasticated chassis and the absorbent core. The void space is coincident with unbonded zones of the core where the core is unbonded to the chassis. The void space is a dynamic void space that is responsive to stretching and contraction of elastics of the elasticated chassis, such that the void space is responsive to movements of a wearer's body when the absorbent article is worn.

Certain aspects of the present disclosure provide for a method of making an absorbent article. The method includes bonding an absorbent core to an elasticated chassis at one or more discrete boding zones, such that the absorbent core is unbonded from the chassis at one or more unbonded zones that are unbonded with the chassis. From 5% to 40% of the surface area of a bottom surface of the core is bonded with the chassis, and from 60% to 95% of the surface area of the bottom surface of the core is unbonded with the chassis.

In some aspects, the method includes forming a void space between the elasticated chassis and the absorbent core. The void space is coincident with unbonded zones of the core where the core is unbonded to the chassis. The void space is a dynamic void space that is responsive to stretching and contraction of elastics of the elasticated chassis.

The foregoing has outlined rather broadly the features and technical advantages of the present disclosure in order that the detailed description that follows may be better understood. Additional features and advantages will be described hereinafter, which form the subject of the claims. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope as set forth in the appended claims. The novel features which are believed to be characteristic of the products, systems, and methods, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

So that the manner in which the features and advantages of the system, products, and/or method so of the present disclosure may be understood in more detail, a more particular description briefly summarized above may be had by reference to the embodiments thereof which are illustrated in the appended drawings that form a part of this specification. It is to be noted, however, that the drawings illustrate only various exemplary embodiments and are therefore not to be considered limiting of the disclosed concepts as it may include other effective embodiments as well.

FIGS. 1A and 1B are plan and expanded perspective views respectively of a first embodiment featuring two zones of bonding between the absorbent core and the underlying material. The bonding zones are towards the front and rear edges of the absorbent core, leaving a large central area of the core unbonded with the underlying material;

FIGS. 2A and 2B are plan and expanded perspective views respectively of a second embodiment featuring one zone of bonding between the absorbent core and the underlying material. The bonding zone is along the central axis of the core, leaving the side edge of the absorbent core unbonded with the underlying material;

FIGS. 3A and 3B are plan and expanded perspective views respectively of a third embodiment featuring three zones of bonding between the absorbent core and the underlying material. The bonding zones are in a central region of the core and towards the front and rear edges of the absorbent core, leaving the side edges of the core and large areas of the mid-front and mid-rear sections of the core unbonded with the underlying material;

FIGS. 4A and 4B are plan and expanded perspective views respectively of a fourth embodiment featuring one zone of bonding between the absorbent core and the underlying material. The bonding zone is in the central region of the core, leaving a large front and rear regions of the core unbonded with the underlying material;

FIGS. 5A and 5B are plan and expanded perspective views respectively of a fifth embodiment featuring two zones of bonding between the absorbent core and the underlying material. The bonding zones are towards side edges in a central region of the core, leaving a central area of the core and large regions of the front and rear parts of the core unbonded with the underlying material;

FIGS. 6A and 6B are plan and expanded perspective views respectively of a sixth embodiment featuring six zones of bonding between the absorbent core and the underlying material. Four of the bonding zones are located in the corners of the absorbent core with two more bonding area in a central region towards each side edge of the core, leaving a large central, mid-front and mid-rear regions of the core unbonded with the underlying material;

FIG. 7 is a cross-section through line A-A in FIG. 1A, showing how the core, when bonded to the gathered or shined elastic surface underneath, is also gathered by the contraction of the elastic material;

FIG. 8 is a cross-section through line A'-A' in FIG. 2A, showing how the core, when partly bonded to the gathered or shirred elastic surface underneath, is gathered by the contraction of the underlying elastic material in the bonded zone, but is less effected by the gathering of the material in the unbonded zone;

FIG. 9A is a cross-section through line A"-A" in FIG. 6A, showing how the core, when partly bonded to the gathered or shirred elastic surface underneath, is gathered by the contraction of the underlying elastic material in the bonded zone, but is less effected by the gathering of the material in the unbonded zone;

FIGS. 10A and 10B are plan and expanded perspective views respectively of a seventh embodiment showing elastic members in the chassis;

FIGS. 11A and 11B are plan and expanded perspective views respectively of an eighth embodiment showing elastic members in the chassis and in the crotch region between a polyethylene film and the chassis;

FIGS. 14A and 14B are plan and expanded perspective views respectively of a twelfth embodiment as a three-piece diaper;

FIGS. 15A and 15B are plan and expanded perspective views respectively of a thirteenth embodiment as a three-piece diaper with elastic members in the crotch region;

FIGS. 17A and 17B are plan and expanded perspective views respectively of an absorbent article featuring one zone of bonding between the absorbent core and the underlying material. The bonding zone is along the central axis of the core, leaving the side edge of the absorbent core unbonded with the underlying material. The bonding zone is located beneath the impermeable layer, rather than above the impermeable layer;

FIG. 20A is a cross-section through line A"-A" in FIG. 6A, showing how the core, when partly bonded to the gathered or shirred elastic surface underneath, is gathered by the contraction of the underlying elastic material in the bonded zone, but is less effected by the gathering of the material in the unbonded zone, opening the void space;

FIG. 20B is a cross-section through line A"-A" in FIG. 6A, showing how the core, when partly bonded to the elastic surface underneath, is extended and stretched by the extension and stretching of the underlying elastic material in the bonded zone, closing the void space;

FIG. 21A is a cross-section through line A"-A" in FIG. 6A, showing forces on the core when gathered or shirred due to contraction of the underlying elastic material in the bonded zone, including showing flow lines for fluid contained within the void space;

FIG. 21B is a cross-section through line A"-A" in FIG. 6A, showing forces on the core when extended and stretched due to stretching of the underlying elastic material in the bonded zone.

Figure 9B:
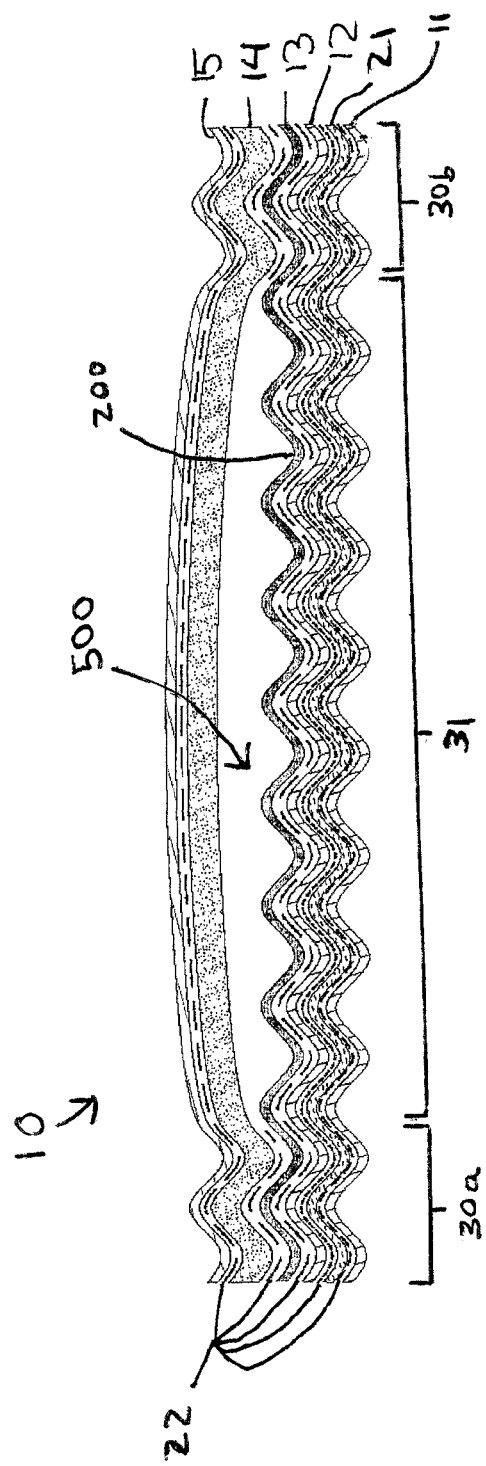
FIG. 9B is an alternative view of a cross-section through line A"-A" in FIG. 6A, showing how the core, when partly bonded to the gathered or shirred elastic surface underneath, is gathered by the contraction of the underlying elastic material in the bonded zone, but is less effected by the gathering of the material in the unbonded zone.

Products and methods according to present disclosure will now be described more fully with reference to the accompanying drawings, which illustrate various exemplary embodiments. Concepts according to the present disclosure may, however, be embodied in many different forms and should not be construed as being limited by the illustrated embodiments set forth herein. Rather, these embodiments are provided so that this disclosure will be thorough as well as complete and will fully convey the scope of the various concepts to those skilled in the art and the best and preferred modes of practice. For example, many of the exemplary descriptions provided herein are concerned with training pants for infants and young children or diapers. Aspects of the concepts described may, however, be equally applicable to designs for and the manufacture of adult incontinence products and other similar products.

DETAILED DESCRIPTION

The foregoing has outlined rather broadly the features and technical advantages of the present disclosure in order that the detailed description that follows may be better understood. Additional features and advantages will be described hereinafter, which form the subject of the claims. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope as set forth in the appended claims. The novel features which are believed to be characteristic of the products, systems, and methods, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Aspects of the present disclosure are particularly suited for, or related to, disposable absorbent articles such as baby diapers, training pants for infants and young children and adult incontinence diapers and pants. Specific embodiments may provide a web of elastic composite, an elastic composite or body, or elastic distribution patterns within these products, which, in turn, may improve the product's fit and comfort, its support and sealing capabilities, enhance the cost and manufacturability of the product and\or enhance the aesthetic qualities of the product.

Disposable absorbent articles contemplated herein include training pants, pull-on diapers, disposable underwear, and adult incontinence garments. As for training pants, these garments are used by young children to facilitate a child's transition from using diapers to wearing regular underpants (i.e., during toilet training). Training pants and other disposable pull-on pants have closed sides such that the user or caregiver raises the garment about the user's legs to wear the garment and slips the garment downward about the user's legs to take it off. These articles and garments are collectively referred to herein as "absorbent pants" or "pants products."

Elastic members may be incorporated into different parts of an absorbent garment. For example, elastic members may be positioned longitudinally along a diaper, generally outboard of the absorbent core to affect a seal around the buttocks, legs, or both of the users. In addition, several elastic members (e.g., in the form of elongated elastic threads or strands) may be positioned laterally throughout the waist regions (including the side waist regions) of an absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of an absorbent garment, that part or area typically becomes a distinct, functional component of the garment. These elastic components include the side panels or ear portions, the waistband, and fastening tabs. Due in part to its multi-component construction, elastic composites may require a dedicated sub-process for manufacture that must be accommodated by the greater garment manufacturing process. Alternatively, the elastic composite may be manufactured independently or simply, manufactured in a separate sub-process detached from the central garment manufacturing system. In either case, a source of the elastic composite may be provided as input to the garment manufacturing process.

U.S. Pat. Nos. 7,462,172 and 7,361,246 and U.S. Pat. Appl. Publ. US 2012/0071852 provide background information on elastic composites (and the manufacture of such composites) of a type relevant to the present disclosure. Accordingly, these patent publications are hereby incorporated by reference and made a part of the present disclosure, but only to the extent that incorporated subject matter provides background information and/or exemplary composites and processes suitable for use on, or with, the present composites, systems, and methods. Thus, the incorporated subject matter shall not serve to limit the scope of the present embodiments.

For purposes of the present description, the terms "elastic composite", "elastic composite body", and "elasticized article" refer to a multi-layer or multi-component construction that incorporates an elastomeric material(s) or elastic member(s). In this construction, a plurality of elastic members, such as threads or strands, are connected to or disposed adjacent one or more materials, e.g., backsheet and topsheet. In this way, the elastic members impart elasticity to the connected or adjacent layers and thus, to that part of the garment or article. Such an elastic structure may be a distinct attachable component of the garment or article, or may be a distinct portion or section of the garment body article or a larger, unitary component of the garment.

Further, as used herein, the term "web" refers to an extended, conveyable sheet or network. The term "substrate" refers to a supporting web, sheet, or layer, such as a web or layer of backsheet onto which elastics adhere or are otherwise supported. Further, a web may be of an elastic composite and/or provide a plurality or series of discrete elastic composite bodies. In embodiments described herein, such elastic composite bodies may be separated from the web to form the basis of a disposable absorbent article such as a diaper or absorbent pants.

The present disclosure is directed, in one aspect, to a combination of a disposable absorbent core and chassis. The disclosure is also directed to a disposable absorbent article or garment including the disposable absorbent core and chassis. In various or further applications, the disposable absorbent article or garment may take the form of a diaper, training pants, adult incontinence product, feminine hygiene product, and other similar disposable absorbent products.

FIGS. 1A and 1B are plan and expanded perspective views respectively of a first embodiment of absorbent article 10. Absorbent article 10 includes chassis 17 and core 18. As described in more detail below, an aspect of certain embodiments is that absorbent components of core 18 are substantially unconnected to elastic components chassis 17, such as elastic/stretchable components of chassis 17 that run laterally across core 18 and that form part of an outer shell of absorbent article 10 (e.g., an outer shell of a diaper).

Chassis 17 includes waist regions 23a and 23b, and crotch region 20. During use, waist regions 23a and 23b may be coupled about a user's waist, such as via adhesive tabs, allowing absorbent article 10 to be worn. In some embodiments, chassis 17 includes outer backsheet layer 11 coupled, such as via adhesive, with inner backsheet layer 12. Chassis 17 may be designed to prevent fluid from passing from core 18 through one or more of outer backsheet layer 11 and inner backsheet layer 12, and out of absorbent article 10. In some embodiments, outer backsheet layer 11 and inner backsheet layer 12 may be formed of a fluid and/or liquid impermeable film (e.g., polyethylene film) that may extend the full width of absorbent article 10, a cloth-like material, or combinations thereof. In some aspects, impermeable layer 13 is replaced with a permeable layer. Outer backsheet layer 11 and inner backsheet layer 12 may have vapor transmission properties ("breathability") that allow vapor to pass through chassis 17 without releasing fluid and/or liquid stored in core 18. Each of outer backsheet layer 11 and inner backsheet layer 12 may be made of a liquid impermeable but vapor transmittable non-woven material such as spunbond, melt-blown (SB) nonwoven; spunbond, melt-blown, spun-bond ("SMS") nonwoven; spun-bond, melt-blown, melt-blown, spun-bond ("SMMS") nonwoven; micro, nano, or splittable fibers; spun melt or spun laced material; carded material; fluid and/or liquid impermeable film (e.g., polyethylene film); or combinations thereof. For example and without limitation, in one embodiment inner backsheet layer 12 is formed of an SB nonwoven, SMS nonwoven, or a polyethylene film, while outer backsheet layer 12 is formed of an SB nonwoven or SMS nonwoven.

In some embodiments, absorbent article 10 includes impermeable layer 13, which may be a polyethylene film. Impermeable layer 13 may be substantially fluid and/or liquid impermeable. Impermeable layer 13 may be coupled, such as via adhesive, with inner backsheet 12.

Impermeable layer 13 may be coupled with absorbent core 14, such as via one or more bonding zones 19a and 19b. As shown in FIGS. 1A and 1B, bonding zones 19a and 19b are located towards lateral edges 24a and 24b (e.g., front and rear edges) of absorbent core 14, leaving a large central area of absorbent core 14 unbonded with the underlying material of chassis 17, here shown as impermeable layer 13. Bonding zones 19a and 19b of FIGS. 1A and 1B are shown as strips approximately extending between longitudinal edges 25a and 25b of absorbent core 14. Bonding zones 19a and 19b may be formed of, for example and without limitation, a hot melt adhesive.

Core 18 may further include topsheet 15 coupled with absorbent core 14, such as via hot melt adhesive, and leg cuffs 16. Leg cuffs 16 may be coupled with topsheet 15, such as via hot melt adhesive, along topsheet longitudinal edges 27, and may extend between topsheet lateral edges 28. Topsheet 15 and leg cuffs 16 may be made of the same or different materials as outer backsheet layer 11 and inner backsheet layer 12.

Chassis 17 includes one or more elastic members 21 (as shown in FIG. 7), such as elastic strands or elastic films, incorporated therein. In operation, when a user wears absorbent article 10, elastic members 21 of chassis 17 may become gathered or shirred, such as when the user walks while wearing absorbent article 10. As shown in FIG. 7, portions of absorbent core 14 that are bonded to portions of chassis 17 having elastic members 21 (e.g., elastic strands or films) that are gathered or shirred are also gathered or shined. Without being bound by theory, it is believed that the bonding between absorbent core 14 and chassis 17 allows for the transference of gathering or shirring from elastic members 21 of chassis 17 to absorbent core 14. Such gathering or shirring of absorbent core 14 may cause discomfort to the user of absorbent article 10. By tailoring the number of and placement of bonding zones 19 between absorbent core 14 and the underlying material of chassis 17, the transference of gathering or shirring due to contraction of elastic members 21 of chassis 17 to absorbent core 14 may be reduced or eliminated.

As shown in FIG. 7, adjacent layers of absorbent article 10 may be bonded with hot melt adhesive 22.

FIGS. 2A and 2B are plan and expanded perspective views respectively of a second embodiment of absorbent core 10 including one bonding zone 19 between absorbent core 14 and chassis 17. Single bonding zone 19 of FIGS. 2A and 2B is located along central axis 29 of absorbent core 14, leaving the side edges of absorbent core 14 unbonded with chassis 17. FIG. 8 is a cross-section through line A'-A' in FIG. 2A, showing how absorbent core 14, when partly bonded to gathered or shined elastic member 21 underneath at bonded region 19, is gathered or shined by the contraction of elastic member 21 in bonded zone 19. Transference of gathering or shining from elastic member 21 to absorbent core 14 is reduced or eliminated in regions of absorbent core 14 that are not bonded to chassis 17, such as unbonded zone 31a and 31b. Core 18 including absorbent core 14 having regions that are not bonded to chassis 17 (e.g., unbonded zone 31a and 31b) may be referred to herein as a "floating core" or "floating absorbent core." As used herein, "floating core" or "floating absorbent core" refers to an absorbent core that is bonded to the underlying layer of absorbent article 10 (here the elasticized chassis 17) at discrete locations, points, and/or areas only. As used herein, "floating" refers to the aspect of the floating absorbent cores where areas of the floating absorbent core are not bonded to the underlying layer of absorbent article 10 such that the unbonded areas of the floating absorbent core are free to move vertically relative to the position of the underlying layer of absorbent article 10. Thus, unbonded zones of the floating absorbent core 14 are said to be "floating." That is, with reference to FIG. 21A, the unbonded areas of floating absorbent core 14 are free to move along directions 950 relative to the elasticated chassis of absorbent article 10. In some aspects, absorbent article 10 includes an absorbent core 14 that is not uniformly or comprehensively bonded to elasticized chassis 17.

In some aspects, a bottom surface 114 (as shown in FIG. 9A) of floating absorbent core 14 includes one or more portions of surface area that are bonded to the elasticated chassis 17 (at bonding zones 19) and one or more portions of surface area that are unbonded (not bonded) to elasticated chassis 17. In some aspects, equal to or less than 90% of the surface area of bottom surface 114 is bonded to elasticated chassis 17 (i.e., is bonded to impermeable layer 13, upper backsheet 12, lower backsheet 11, elastic member 21, or any other portion of chassis 17 residing below floating absorbent core 14 and/or below void space 500) based on the total surface area of the bottom surface 114. In certain aspects, equal to or less than 85%, equal to or less than 80%, equal to or less than 75%, equal to or less than 70%, equal to or less than 65%, equal to or less than 60%, equal to or less than 55%, equal to or less than 50%, equal to or less than 45%, equal to or less than 40%, equal to or less than 35%, equal to or less than 30%, equal to or less than 25%, equal to or less than 20%, equal to or less than 15%, equal to or less than 10%, or equal to or less than 5% of the surface area of bottom surface 114 is bonded to elasticated chassis 17, based on the total surface area of bottom surface 114. The percentage of bottom surface 114 that is bonded to elasticated chassis 17 may range from about 5% to about 90%, from about 10% to about 80%, from about 20% to about 70%, from about 30% to about 60%, from about 40% to about 50%. In certain aspects, the percentage of bottom surface 114 that is bonded to elasticated chassis 17 ranges from 10% to 30%. In each case, the remainder of the surface area of bottom surface 114 is unbonded to elasticated chassis 17. For example, if 10% to 30% of the surface area of bottom surface 114 is bonded to elasticated chassis 17, then 70% to 90% of the surface area of bottom surface 114 is unbonded to elasticated chassis 17.

FIGS. 3A and 3B are plan and expanded perspective views respectively of a third embodiment of absorbent article 10 including three bonding zones 19a, 19b, and 19c located between absorbent core 14 and the underlying material of chassis 17. Bonding zones 19a-19c of FIGS. 3A and 3B are located in a central region of core 18, including two located towards lateral edges 24a and 24b and one located at a center of core 18, leaving longitudinal edges 25a and 25b of core 18 and large areas of the mid-front and mid-rear sections of core 18 unbonded with the underlying material of chassis 17.

FIGS. 4A and 4B are plan and expanded perspective views respectively of a fourth embodiment of absorbent article 10 including a single bonding zone 19 between absorbent core 14 and the underlying material of chassis 17. Bonding zone 19 of FIGS. 4A and 4B is located in the central region of core 18, leaving a large front and rear region of core 18 unbonded with the underlying material of chassis 17.

FIGS. 5A and 5B are plan and expanded perspective views respectively of a fifth embodiment of absorbent article 10 including two bonding zones 19a and 19b between absorbent core 14 and the underlying material of chassis 17. Bonding zones 19a and 19b of FIGS. 5A and 5B are located towards longitudinal edges 25a and 25b in a central region of core 18, leaving a central area of core 18 and large regions of the front and rear parts of core 18 unbonded with the underlying material of chassis 17.

FIGS. 6A and 6B are plan and expanded perspective views respectively of a sixth embodiment of absorbent article 10 including six bonding zones 19a-19f of bonding between absorbent core 14 and the underlying material of chassis 17. Four bonding zones, bonding zones 19a, 19b, 19e and 19f, are located in the corners of absorbent core 14. Two bonding zones, bonding zones 19c and 19d, are located in a central region of absorbent core 14 towards longitudinal edges 25a and 25b of core 18, leaving large central, mid-front and mid-rear regions of core 18 unbonded with the underlying material of chassis 17. FIG. 9A is a cross-section through line A"-A" in FIG. 6A, showing how absorbent core 14, when partly bonded to gathered or shined elastic member 21 thereunder, is gathered by the contraction of elastic member 21 in bonded zone 19a and 19b. Transference of gathering or shirring due to contraction of elastic member 21 to absorbent core 14 is reduced or eliminated in regions of absorbent core 14 that are not bonded to chassis 17, such as unbonded zone 31.

FIG. 9B is an alternative depiction of a cross-section through line A"-A" in FIG. 6A. As shown in FIG. 9B, in some aspects bonding between elastic member 21 and layers enclosing elastic member 21, here shown as outer backsheet layer 11 and inner backsheet layer 12, is continuous. In contrast, as shown in FIG. 9A, in other aspects bonding between elastic member 21 and enclosing elastic member 21, here shown as outer backsheet layer 11 and inner backsheet layer 12, is discontinuous (e.g., intermittent), forming channels 100 between elastic member 21 and the enclosing layers, outer backsheet layer 11 and inner backsheet layer 12, such that no channels are formed between elastic member 21 and the enclosing layers. In certain aspects, void space 500 directs liquid contained therein away from the target area (area of insult where extrudate first absorbs into absorbent core 14) where, often, the most amount of liquid is resident in the absorbent core 14. For example, a void space 500 having longitudinally-oriented tubes (i.e., fluid channels 200), would direct liquid contained therein longitudinally along such tubes. In some aspects, at least one side of void space 500 is not sealed. In some aspects, at least one side of void space 500 is sealed. For example, for a void space 500 having longitudinally-oriented tubes (i.e., fluid channels 200), the longitudinal edges of such a void space 500 may be sealed or relatively sealed, whereas, the ends of the void space 500 (i.e., the edge of the void space 500 at the end of the tubes (fluid channels)) may be unsealed.

By tailoring the number of and placement of bonding zones 19 between absorbent core 14 and the underlying material of chassis 17, the transference of gathering or shining due to contraction of elastic members 21 of chassis 17 to absorbent core 14 may be reduced or eliminated.

FIGS. 10A and 10B are plan and expanded perspective views respectively of a seventh embodiment of absorbent article 10. Chassis 17 may include one or more elastic members 21*a* and 21*b* in waist regions 23*a* and 23*b* of absorbent article 10, and one or more elastic members 21*c* and 21*d* in crotch region 20 of absorbent article 10. As shown, absorbent core 14 is coupled with chassis 17 via bonding zones 19*a* and 19*b* at regions of chassis that do not include elastic members 21*a*-21*d*.

FIGS. 11A and 11B are plan and expanded perspective views respectively of an eighth embodiment of absorbent article 10. Absorbent article 10 in FIGS. 11A and 11B are identical to that in FIGS. 10A and 10B, except that the embodiment shown in FIGS. 11A and 11B additionally includes one or more elastic members 21*e* under core 18 in crotch region 20 of absorbent article 10. Elastic members 21*e* may be straight, linear elastic strands, as shown, or may be curvilinear. Elastic members 21*e* may be located in a variety of places within absorbent article 10. As shown, elastic members 21*e* are located between impermeable layer 13 and outer backsheet layer 11. Elastic members 21*e* of core 18 may be isolated from all elastic members 21*a*-21*d* of chassis 17. As used herein, "isolation" of elastic members 21*e* of core 18 from all elastic members 21*a*-21*d* of chassis 17 refers to the arrangement of elastic members 21*a*-21*e*, such that elastic members 21*e* are not in contact with elastic members 21*a*-21*d* of chassis 17, do not intersect elastic members 21*a*-21*d* of chassis 17, or combinations thereof. With elastic members 21*e* isolated from elastic members 21*a*-21*d*, elastic members 21*e* are not elastically coupled with elastic members 21*a*-21*d*. As used herein "elastically coupled" refers to the ability of elastic members 21*a*-21*d* to transfer elastic effects (e.g., stretching, contracting, shining, gathering, or the like) to other elements of absorbent article 10.

Figure 12B:
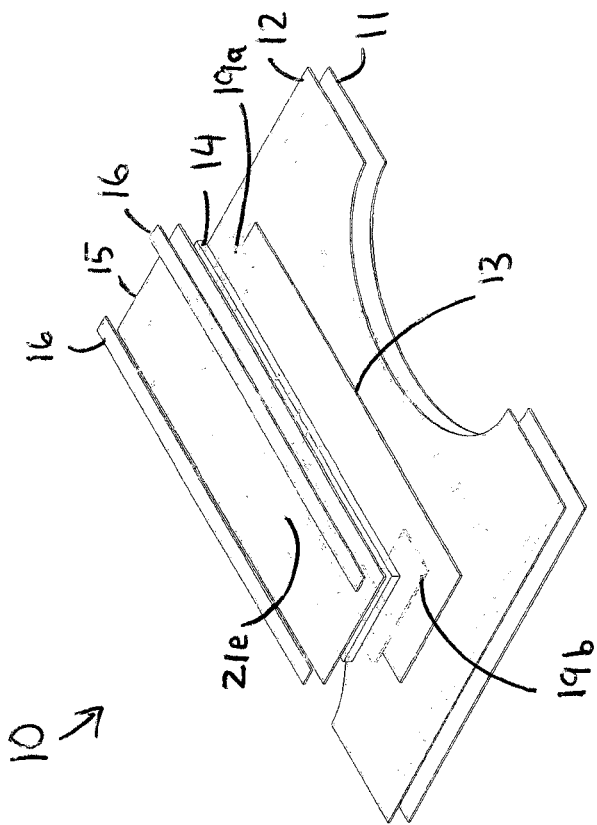
FIGS. 12A and 12B are expanded perspective views respectively of a ninth and tenth embodiments showing elastic members in the chassis and in the crotch region between the polyethylene film and the absorbent core and between the absorbent core and the topsheet, respectively.
Figure 12A:
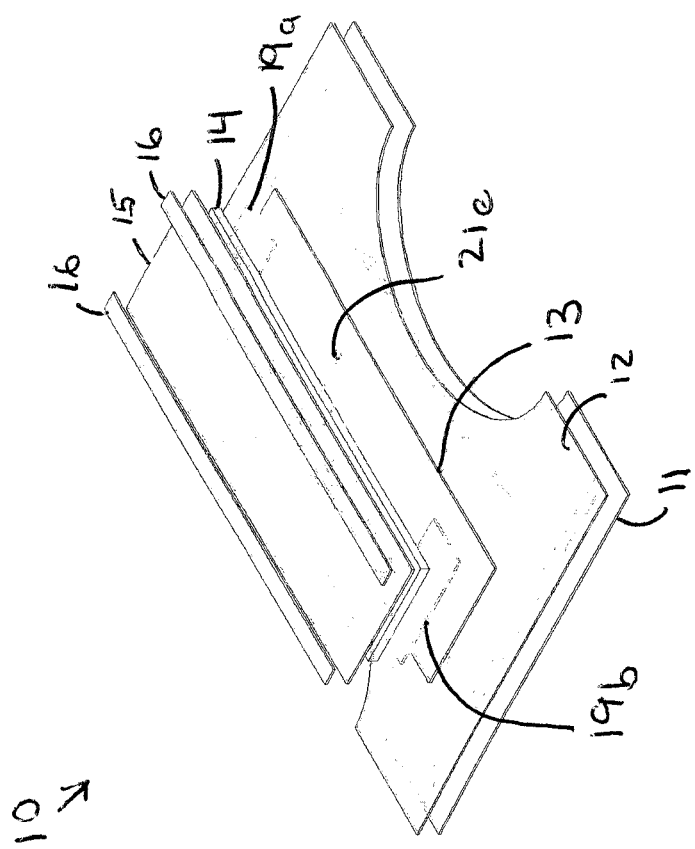

FIGS. 12A and 12B are expanded perspective views of ninth and tenth embodiments of absorbent article 10. Absorbent article 10 in FIGS. 12A and 12B are identical to that in FIGS. 11A and 11B, except for the location of elastic members 21*e*. In FIG. 12A, elastic members 21*e* are located between impermeable layer 13 and absorbent core 14. In FIG. 12B, elastic members 21*e* are located between absorbent core 14 and topsheet 15. The configuration of elastic members 21*e* shown in FIG. 12B is suitable for use in an Oyster Elastic Core.

Figure 13:
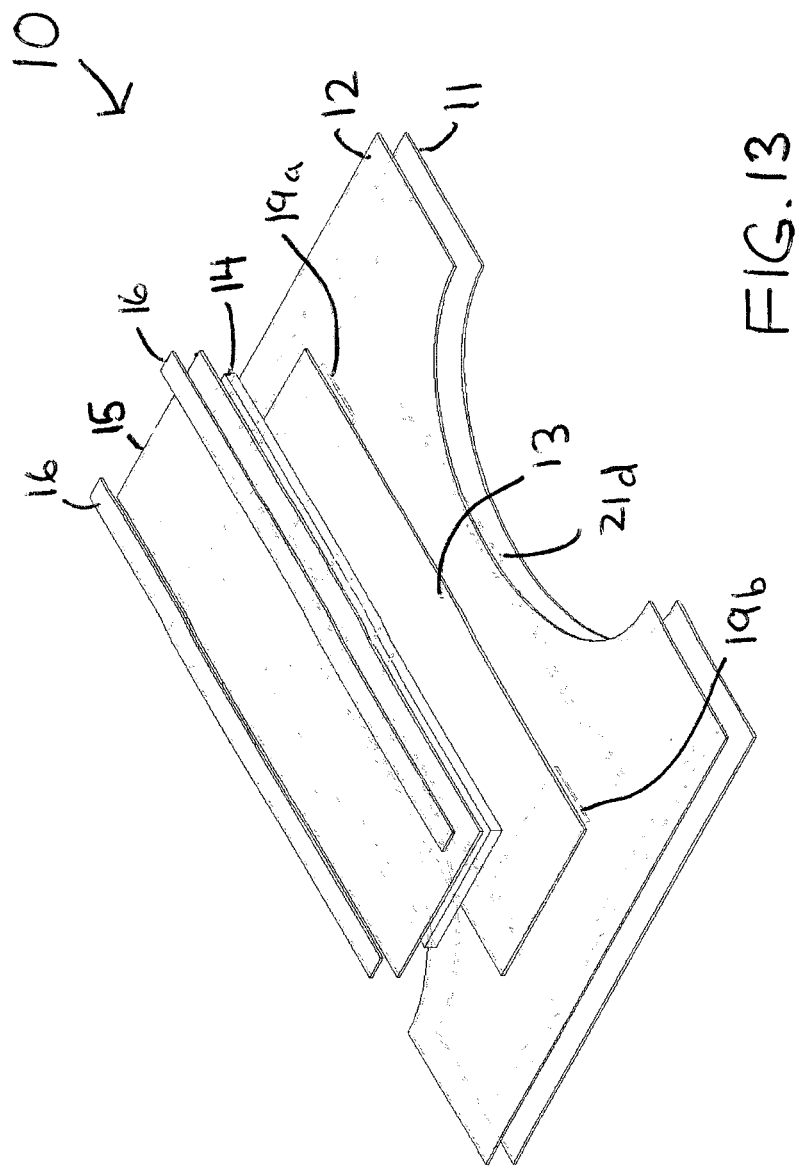
FIG. 13 is an expanded perspective view respectively of an eleventh embodiment showing bonding zones of the core between the polyethylene film and chassis.

FIG. 13 is an expanded perspective view of an eleventh embodiment of absorbent article 10. Absorbent article 10 in FIG. 13 is identical to that in FIG. 12B, except for the location of bonding zones 19*a* and 19*b*. In FIG. 13, bonding zones 19*a* and 19*b* are located between fluid impermeable layer 13 and inner backsheet layer 12, whereas, in FIG. 12B bonding zones 19*a* and 19*b* are located between absorbent core 14 and impermeable layer 13.

Bonding zones 19 may be located in various configurations and regions within absorbent article 10 between all elastic members 21 of chassis 17 and absorbent core 14, such that shining, stretching, and other elastification effects of elastic members on chassis 17, is not directly or completely transferred to absorbent core 14.

FIGS. 14A and 14B are plan and expanded perspective views respectively of a twelfth embodiment of absorbent article 10. As shown, absorbent article is a three-piece diaper having front chassis 17*a* forming a front waistband, rear chassis 17*b* forming a rear waistband, and core 18. Front chassis 17*a* includes elastic member 21*a*, rear chassis 17*b* includes elastic member 21*b*, and impermeable layer 13 includes elastic member 21*c* and 21*d*. The configuration of absorbent article 10 shown in FIGS. 14A and 14B is suitable for use as a pant diaper, for example. Use of discrete, selected bonding zones 19*a* and 19*b* between absorbent core 14 and other portions of core 18 (e.g., impermeable layer 13) allows for elastification effects on absorbent core 14 (e.g., transference of stretching, shining or gathering) to be reduced or eliminated.

FIGS. 15A and 15B are plan and expanded perspective views respectively of a thirteenth embodiment of absorbent article 10. Absorbent article 10 shown in FIGS. 15A and 15B is identical to that shown in FIGS. 14A and 14B, except that absorbent article 10 in FIGS. 15A and 15B additionally includes one or more elastic members 21*e* between absorbent core 14 and topsheet 15.

In embodiments, absorbent core 14 may be substantially unconnected to elastic members 21 of chassis 17, in particular elastic members 21 of chassis 17 that run laterally across core 18 and that form part of the outer shell of absorbent article 10. For example and without limitation, absorbent core 14 may be bonded to components of chassis 17 only in discrete bonding zones 19, forming bonded zone 19, and not bonded to chassis 17 in other zones, forming unbonded zones 31. In some embodiments, each bonding zone 19 may have a smaller surface area than the sum of surface areas of all unbonded zones 31 of absorbent article 10. In some embodiments, the sum of the surface areas of all bonding zones 19 of absorbent article 10 may be smaller than the sum of the surface area of all unbonded zones 31 of absorbent article 10. For example and without limitation, an embodiment with absorbent core 14 having a surface area of 400 mm×100 mm may have two bonding zones 19*a* and 19*b* at the front and rear longitudinal ends of absorbent article 10 (e.g., as shown in FIGS. 1A and 1B) that each have a surface area of 30 mm×100 mm, and may have unbonded zone 31 with a surface area of 340 mm×100 mm between bonding zones 19*a* and 19*b*. Alternatively, an embodiment of absorbent article 10 may have a centrally located bonding zone 19 in the form of a strip (e.g., as shown in FIGS. 2A and 2B) having a surface area of 400 mm×5 mm, and have two unbonded zones 31*a* and 31*b* each having a surface area of 400 mm×47.5 mm.

In some embodiments, core 18 and/or absorbent core 14 may be an integral, continuous, single-piece structure, such that core 18 and/or absorbent core 14 is of self-supporting between bonded zones 19 and unbonded zones 31. For example and without limitation, core 18 and/or absorbent core 14 may be an Oyster core or a Dry MT core. In other embodiments, core 18 and/or absorbent core 14 may be a pulp/super absorbent polymer (SAP) core. In embodiments that core 18 and/or absorbent core 14 are a pulp/SAP core, the pulp/SAP core may be wrapped and/or enclosed in a support structure, such as a nonwoven, before being bonded to chassis 17. In some embodiments, the composition of core 18 and/or absorbent core 14 may be formulated to provide regions of core 18 and/or absorbent core 14 that function as stiffeners. For example, certain regions of core 18 and/or absorbent core 14 may be provided with more absorbent particles (e.g., SAP) or a higher density absorbent material. In some embodiments, such regions of core 18 and/or absorbent core 14 may include particles, fibers, or other material layers that increases the density, thickness, and/or hardness of that region of core 18 and/or absorbent core 14. In some embodiments, hot melt adhesive 22 may be provided in or on core 18 and/or absorbent core 14. In some embodiments, target regions of core 18 and/or absorbent core 14 may include an increased amount of hot melt adhesive 22 relative to other regions of core 18 and/or absorbent core 14. In certain embodiments, core 18 and/or absorbent core 14 may be composed of pockets and/or aggregates of SAP, as is known in the art. The shape and size of such pockets and/or aggregates, as well as the composition thereof, may be varied in different regions of core 18 and/or absorbent core 14 to achieve desired stiffness and bending characteristics, as is known in the art. The pocket patterns, as determined by the bonding patterns, may be designed to achieve the desired stiffness properties. Furthermore, the bonding method (e.g., point bonding, solid bonding, etc.) may also be varied. Such pockets and/or aggregates may be made in accordance with methods known to those skilled in the art, such as the methods described in U.S. Pat. Appl. Publ. US 2014/0303582 A1 and U.S. Pat. No. 8,148,598, which are incorporated herein in their entirety.

In use, when elastic members 21 of chassis 17 are stretched, extended or relaxed, the surface topology and shape of absorbent core 14 may be substantially unchanged, particularly in unbonded zones 31; as shining of core 18 when elastic members 21 of chassis 17 are relaxed may be reduced or eliminated, and flattening of core 18 when elastic members 21 of chassis 17 are extended may be reduced or eliminated. Thus, in use of at least some embodiments, the shape and surface topology of core 18 may remain generally unchanged. The shape and surface topology of chassis 17 may dynamically change during use, while the shape and surface topology of core 18 may be static or substantially static during use.

In some embodiments, additional elastics or stretchable components (e.g., elastic members 21e) may be incorporated into and/or connected absorbent core 14 to provide a desired shape thereto. In such embodiments, the stretch characteristics of such additional elastics or stretchable components may be independent or substantially independent of chassis 17 stretch characteristics (e.g., independent or substantially independent of elastics or stretchable components of chassis 17).

Figure 16A:
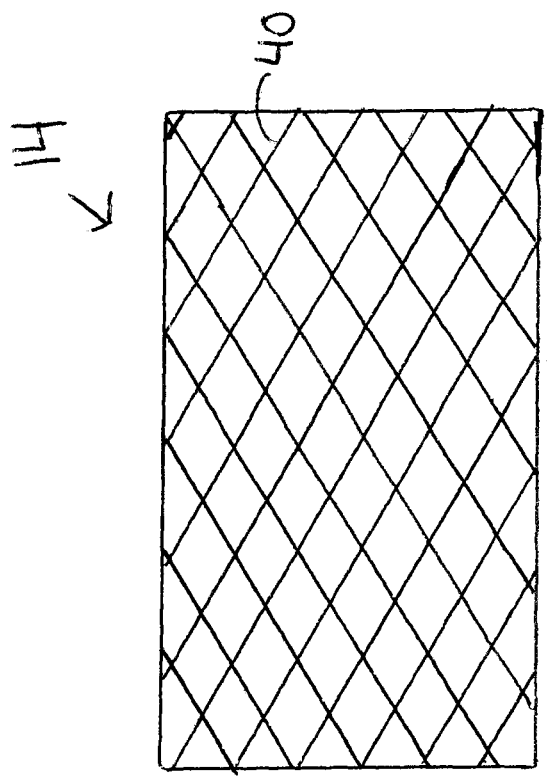
FIG. 16A is a plan view of an embodiment of an absorbent core having an embossed pattern.
Figure 16B:
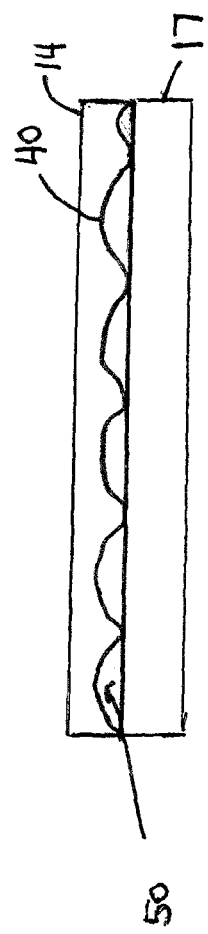
FIG. 16B is a side view of an embodiment of an absorbent core having an embossed pattern coupled with a chassis, forming channels.

In some embodiments, the underside of core 18 and/or absorbent core 14 may have an embossed pattern. In such embodiments, the embossed pattern may create or assist in creation of channels (e.g., small capillary channels or larger channels) located between core 18 and/or absorbent core 14 and the underlying structure (i.e., chassis 17 or component thereof). For example and without limitation, FIG. 16 shows an embodiment of absorbent core 14 having embossed pattern 40. FIG. 16B shows an embodiment of absorbent core 14 with embossed pattern 40 bonded to chassis 17, forming channels 50.

In some embodiments, the material underlying core 18 (i.e., chassis 17 or portions thereof) may have modified wettability characteristics, forming a wettable surface. For example, chassis 17 or portions thereof (e.g., inner backsheet layer 12 and/or outer backsheet layer 11) may be modified to be more hydrophilic or more hydrophobic, such as by treatment thereof with surfactants, corona treatment, or other surface treatments. Modification of wettability characteristics of chassis 17 may encourage fluid flow between core 18 and chassis 17. Hydrophobic treatments of chassis 17 in certain zones may slow down or block fluid flow, such as at the sides or ends of the core 18. As used herein a "wettable surface" is a surface capable having liquid barrier properties, such as a material that has been modified by corona or plasma treatment of the surface, and that allows for fluid distribution thereon.

Void Space

In some aspects, unbonded zones of floating absorbent core 14 include a degree of "free width", a degree of "free length", and a degree of "free area" that is free to move vertically (i.e., along axis 950 as shown in FIG. 21A), laterally, or longitudinally relative to the position of the underlying layer of absorbent article 10 (i.e., the elasticated chassis 17). Such unbonded zones of the floating absorbent core 14 are said to be "floating." For the purposes of illustration, and without limitation, the "free width", "free length" and "free area" will be described with reference to the Figures.

With reference to FIGS. 10A and 10B, core 14 has an average length (longitudinal extent), as identified by reference numeral 1000. However, only a portion of length 1000 is unbonded from chassis 17, specifically unbonded length 2. Unbonded length 2 may be, for example and without limitation, up to or equal to 80% approximately of length 1000. That is, if length 1000 were 10 inches, unbonded length 2 would be 8 inches. Two portions, on either end of core 14, are bonded via bonding zones 19a and 19b, are identified as bonded length 3. Along bonded length 3, core 14 may be 100% or approximately 100% restrained from vertical movement relative to chassis 17. However, along unbonded length 2, core 14 may be approximately 95% or greater unrestrained relative to chassis 17, that is free to move vertically relative to chassis 17. Thus, along about 80% the length of the core 14, the core has about 95% or greater free width and the core in this area is free to move relative to chassis 17, and along about 20% the length of the core 14, the core has about 0% free width. As is clear from FIG. 10A, the lateral width of core 14 coincident with bonding zones 19a and 19b would have about 0% free width and length, and the lateral width of core 14 not coincident with bonding zones 19a and 19b would have about 95% or greater free width (e.g., there is some adherence of the core to the topsheet and chassis 17 along the edges thereof as shown in FIG. 7).

With reference to FIGS. 17A and 17B, core 14 has an average width (lateral extent), as identified by reference numeral 2000. However, only two portions of width 2000 are unbonded from chassis 17, specifically unbonded widths 7. Unbonded widths 7 may together be, for example and without limitation, approximately 85% of width 2000, such that each unbonded width 7 is approximately 42.5% of width 2000. That is, if width 2000 were 10 inches, each unbonded width 7 would be 4.25 inches. One portion in the center of core 14 is bonded via bonding zones 19, and is identified as bonded width 5. Along bonded width 5, core 14 may be 100% or approximately 100% restrained from vertical movement relative to chassis 17. However, along unbonded widths 7, core 14 may be approximately 95% unrestrained relative to chassis 17, that is free to move vertically relative to chassis 17. Thus, along 100% of the length of core 14, the free or unbonded width is at least 85% of the width of the core 14.

Thus, each portion of "free width" of the core 14 is a percentage of the total width of the core 14 that is free to move vertically relative to the underlying elasticated chassis 17. Each portion of free width may be free of bond zones across the extent thereof. One skilled in the art would understand that similar calculations and/or approximations regarding the amount of unbonded length and/or width of each embodiment of core 14 (e.g., the embodiments shown in FIGS. 3A, 4A, 5A, and 6A) may be performed to determine the extent of the length and width of the core 14 that is free to move vertically with respect to the underlying elasticated chassis 17 in order to determine portion free width of each core. In some aspects, the core 14 has an unbonded free width that is at least 50%, at least 60%, at least 70%, at least 80%, at least 90%, or at least 95% of the total width of the core, along a core length equal to or greater than about 50%, 60%, 70%, 80%, 90%, or 95% of the total length of the core. In some aspects, the core 14 has an unbonded free width that range from 50% to 95% of the total width of the core, along a core length that ranges from 50% to 95% of the total length of the core.

With reference to FIG. 3A, at the three bonding zones 19a-19c, the free width is up to or equal 80% of the core width. In between the bonding zones 19-19c, the free width is greater than 95% of the core width. The longitudinal lengths of each bonding zone 19a-19c make up about 3% of the core length. So, the core 14 may be described as having a free width up to or equal 80% for the first 3%, then a free width greater than 95% for the next 45.5% of the core length, a free width up to or equal 80% again for the next 3% of the core length, then a free width greater than 95% for the next 45.5% of the core length, and, finally, a free width up to or equal 80% for the final 3% of the core length. Alternatively, the core 14 may also be described as having a free width greater than 80% for 100% of the core length or greater than some average free width (between 80% and 95%, and probably greater than 90%).

With reference to FIG. 4A, one bonding zone 19 centered about the core 14 has a length that is about 10% of the core length. The core 14 may be described as having a free width greater than 95% along 45% of the core length on either side of the bonding zone 19. Conversely, the core 14 may be described as having a free length equal or up to 90% along 100% of the core width.

With reference to FIG. 6A, the core 14 is bonded at three pairs of bonding zones 19a-19c, each bonding zone having a width of about 10% of the core width. Each bonding zone 19a-19c has a length equal to about 5% of the core length. So, the core 14 may be described as having a free width up to 80% for 5% of the core length, then greater than 95% for 42.5% of the core 14.

With reference to FIG. 4A, the absorbent core 14 may have at least one "free area" that is free to move relative to the underlying chassis 17. As shown in FIG. 3A, core 14 has two free areas 3000. However, one skilled in the art would understand that core 14 may have more or less than two free areas. For example, FIG. 1A depicts a core 14 that has only one free area. Each free area is coincident with an unbonded zones of core 14. Within the boundaries of each free area 3000, there are no bonding zones restraining movement of core 14 relative to chassis 17. Within the boundaries of free areas 3000, core 14 is uniformly unbonded or comprehensively unbonded to chassis 17. In some aspects, the core 14 has an amount of unbonded free area that is greater than 50%, or greater than 60%, or greater than 70%, or greater than 80%, or greater than 90%, or greater than 95% of the total surface area of the bottom surface 114 of the core 14. For example, a core having a total bottom surface area of 50 square inches, and having an unbonded free area that is 50% of the total area of the core, would have an unbonded free area that is 25 square inches.

In some aspects, a void space is formed between the unbonded, floating portions of the absorbent core 14 and the chassis 17 of the absorbent article 10. Such void spaces will be coincident with the free areas, free widths, and/or free lengths of core 14. Void space 500 is shown in FIGS. 8, 9A and 9B.

With reference to FIGS. 9A and 9B, void space 500 is formed between two layers of absorbent article 10, specifically between absorbent core 14 and impermeable layer 13. Void space 500 is not limited to being positioned between absorbent core 14 and impermeable layer 13, and may be positioned between other adjacent layers of absorbent article 10, such as between impermeable layer 13 and a layer of chassis 17, such as inner backsheet layer 12, as shown and described in more detail below with reference to FIGS. 17A and 17B. Void space 500 may be positioned opposite body side 300 of absorbent article 10. As used herein, body side 300 of absorbent article 10 is the side of absorbent article 10 facing the crotch region of the user's body when absorbent article 10 is being worn by the user. In some aspects, there is no layer positioned between the bottom surface 114 of floating absorbent core 14 and void space 500. In other aspects, impermeable layer 13 is the only layer positioned between the bottom surface 114 of floating absorbent core 14 and void space 500.

The configuration and arrangement of void space 500, including the shape, size, and volume of void space 500, is defined, at least in part, by the positions and arrangements of the bonding between the layers of absorbent article 10 (e.g., the positions and arrangements of bonded zones 19). Absorbent article 10 may include a single void space or multiple void spaces, located at any of various positions between layers of absorbent article 10. FIGS. 9A and 9B depict absorbent article 10 having a single, generally centrally located void space 500. FIG. 8 depicts absorbent article 10 having two void spaces 500, each located generally spaced apart from the center of absorbent article 10 and along longitudinal edges 25a and 25b of absorbent core 14. In some aspects of absorbent articles that include multiple void spaces, at least some of the multiple void spaces are in direct fluid communication with other of the multiple void spaces. In other aspects of absorbent articles that include multiple void spaces, each of the multiple void spaces are in fluidically isolated from (i.e., not in fluid communication) with other of the multiple void spaces. For example, bonding zones 19 may seal each of the multiple void spaces from the other of the multiple void spaces.

Void Space—Fluid Distribution and Ventilation

In some such aspects, void space 500 provides for fluid distribution for liquid, gas, or both liquid and gas within absorbent article 10. Fluid (liquid or gas) may enter void space 500 from absorbent core 14, and may travel within void space 500 to other portions of absorbent article 10. For example, liquid may exit a saturated portion of absorbent core 14 and flow within void space 500 to a less saturated portion of absorbent core 14, and may be reabsorbed into absorbent core 14 at the less saturated portion thereof.

In some aspects, void space 500 has a configuration (e.g., shape) such that liquid within void space is directed to and/or towards a desired location within absorbent article 10. For example, void space 500 may extend longitudinally, laterally, or combinations thereof for directing liquid flow therein longitudinally, laterally, or both. Void spaces 500 shown in FIG. 8 may direct fluid flow to longitudinal edges of absorbent article 10, whereas, the void space formed via absorbent article 10 of FIGS. 4A and 4B may direct fluid flow to lateral edges of absorbent article 10.

With further reference to FIGS. 8, 9A, and 9B, in some aspects fluid channels 200 are formed within void space 500. Fluid channels 200 may be formed via elastic forces acting upon chassis 17 (i.e., gathering and/or shirring of upper backsheet 12, lower backsheet 11, and impermeable layer 13. Such gathering and/or shining may result in the formation of the peaks 201 and valleys in the layers forming the chassis 17, wherein the valleys are fluid channels 200. Such fluid channels 200 may function to direct fluid flow within void space 500 to a desired location within absorbent article 10.

As such, void space 500 may function to assist in the distribution of fluids throughout absorbent article 10. Void space 500 may also function as a fluid retention zone of absorbent article 10. For example, if absorbent core 14 is saturated, void space 500 may, in some aspects, provide additional volume capacity for retention of fluids within void space 500.

Void space 500 may also provide for ventilation of gas from and through absorbent article 10. Such ventilation of gas from and/or through absorbent article 10 may promote the drying of absorbent article 10 or at least of absorbent core 14.

In some aspects, the profile of void space 500 may dictate, or at least affect, the profile of absorbent core 14 positioned there-above. As such, the profile of void space 500 may direct and/or influence the fluid retention and/or fluid distribution functions of absorbent core 14.

Void Space—Improvement of Fit

In some aspects, the provision of void space 500 within absorbent article 10 provides an absorbent article with an improved fit to a user's body, when worn, relative to an otherwise identical absorbent article that lacks such a void space. For example, an absorbent article with a floating absorbent core and associated void space, as described herein, may result in a generally flatter absorbent core and topsheet of the absorbent article positioned against the user's body, relative to example, an otherwise identical absorbent article without a floating absorbent core and associated void space.

Void Space—Beneath Impermeable Layer

With reference to FIGS. 17A and 17B, absorbent article 10 is depicted in which bonding zone 19 is positioned below impermeable layer 13, between impermeable layer 13 and outer chassis 17; more specifically between impermeable layer 13 and upper backsheet 12. In such aspects, impermeable layer 13 is floating and elastically isolated from chassis 17 in the same manner as described herein with respect to the floating and elastically isolated absorbent core 14.

In some such aspects, impermeable layer 13 will hinder and/or impede the passage of liquid into void space 500, resulting in a reduction and/or elimination of liquid passage through impermeable layer 13 into void space 500. Thus, in some such aspects, with void space 500 positioned between impermeable layer 13 and upper backsheet 12, void space 500 will either provide reduced fluid retention and/or fluid distribution properties in comparison to aspects with void space 500 positioned between absorbent core 14 and impermeable layer 13, or void space 500 with have no fluid retention and/or fluid distribution properties.

In some such aspects, with void space 500 positioned between impermeable layer 13 and upper backsheet 12, void space 500 will provide for an improved fit, ventilation of gas and associated drying of absorbent article 10 or at least absorbent core 14, or combinations thereof, as discussed elsewhere herein.

In some aspects, with void space 500 positioned between impermeable layer 13 and outer chassis 17, impermeable layer 13 is not elasticated and/or is elastically isolated from chassis 17. Thus, in some such aspects, impermeable layer 13 is not gathered, contracted or shirred when elastic member 21 of chassis 17 is contracted, or is at least less gathered, contracted or shined, when elastic member 21 of chassis 17 is contracted in comparison to otherwise identical absorbent articles in which the void space is positioned between absorbent core 14 and impermeable layer 13 and impermeable layer 13 is elasticated and/or is not elastically isolated from chassis 17.

With void space 500 positioned between impermeable layer 13 and outer chassis 17, absorbent core 14 may be smoother and/or less wrinkled and more comfortable to wear in comparison to an otherwise identical absorbent article in which void space 500 positioned between absorbent core 14 and impermeable layer 13.

Furthermore, in some such aspects, resistance between impermeable layer 13 and nonwoven layer or other layers of outer chassis 17 (e.g., upper backsheet 12) is alleviated; thereby, allowing absorbent core 14 to more easily "float" above chassis 17 and/or providing absorbent core 14 with an increase freedom of movement than in otherwise identical absorbent articles in which void space is not positioned between impermeable layer 13 and chassis 17.

Aspects having a "floating" impermeable layer 13 exhibit minimal contraction and/or gathering of impermeable layer 13 caused by connection with elastics of outer chassis 17. Additionally, in some such aspects, all layers connected above impermeable layer 13 (e.g., topsheet 15 and absorbent core 14) will also exhibit reduced or eliminated contraction and/or gathering and/or shining. Reduction or elimination of such contraction, gathering, and/or shirring results in absorbent core 14 having a generally flatter bodyside surface (flatter presentation) when worn against a user's body, as well as a generally flatter topsheet 15 when worn against the user's body.

In such embodiments, the elasticated outer chassis 17 is free to contract and fit to the anatomy of the wearer while the surface of absorbent article 10 (topsheet 15 and core 14) remain unaffected, or are less affected, by the elastication of outer chassis 17, such that topsheet 15 and core 14 remain generally flat against the wearer's body.

Void Space—Dynamic Properties

In some aspects, void space 500 exhibits dynamic properties, including, but not limited to, a dynamic volume, a dynamic shape, dynamic fluid distribution properties, dynamic fluid retention properties, dynamic ventilation and absorbent core drying properties, or combinations thereof. As used herein, "dynamic properties" refers to properties that dynamically vary. For example, such dynamic properties may vary with the interaction between void space 500 configuration and the user's body movement and forces acting upon absorbent article 10. That is, void space 500 and absorbent core 14 are dynamically responsive to body movements and to external forces, including torsional and compressive forces, and elastic forces.

Figure 18A:
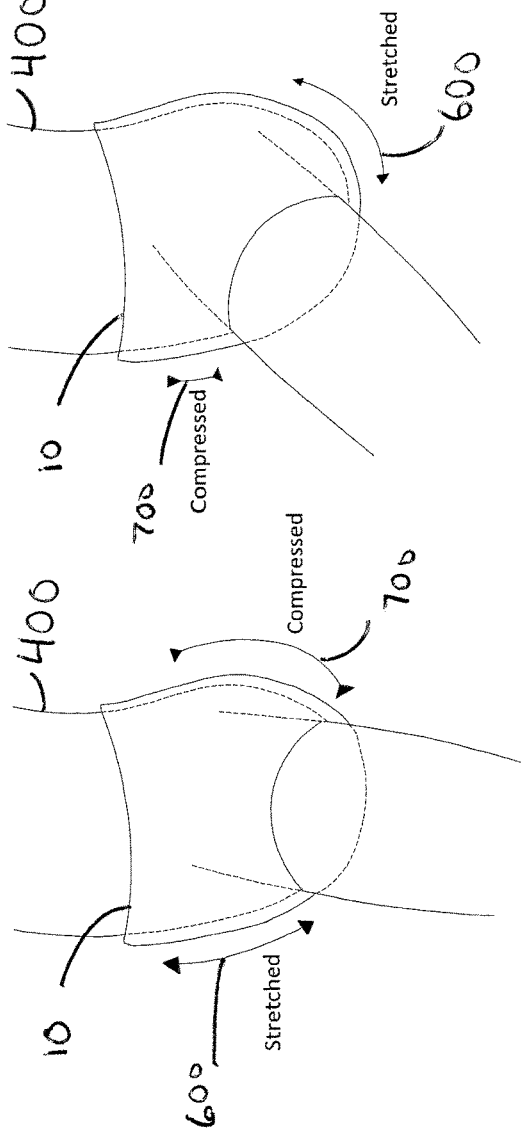
FIGS. 18A-18C are side views showing movements of a wearer of the absorbent article, including the forces exerted upon the absorbent article as a result of such movements.
Figure 18B:
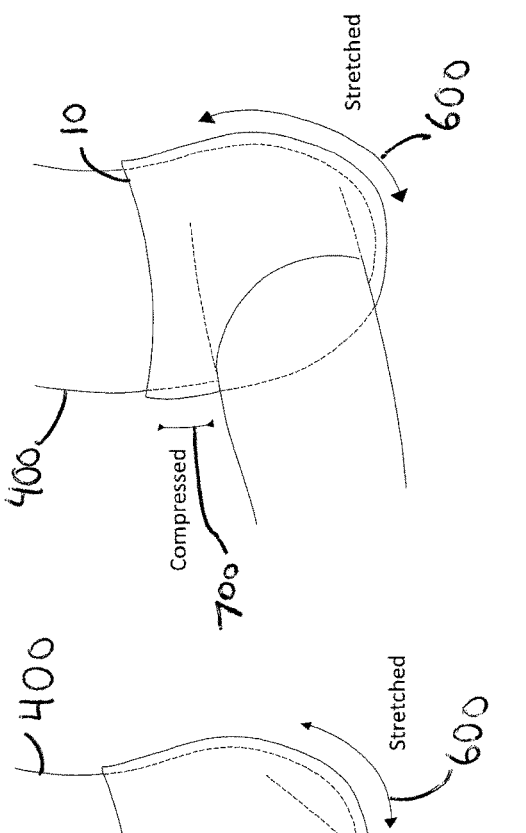
Figure 18C:
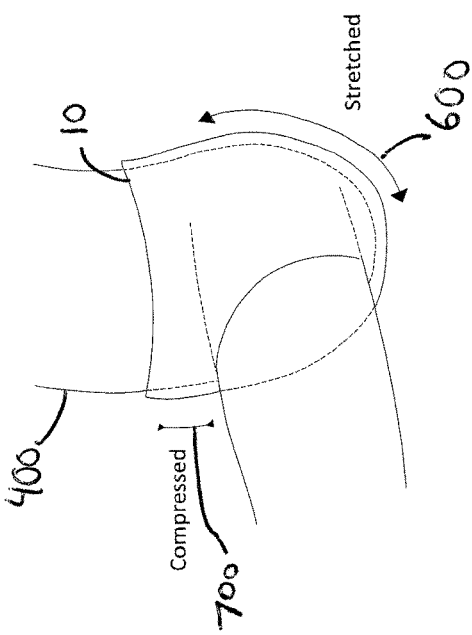
Figure 19A:
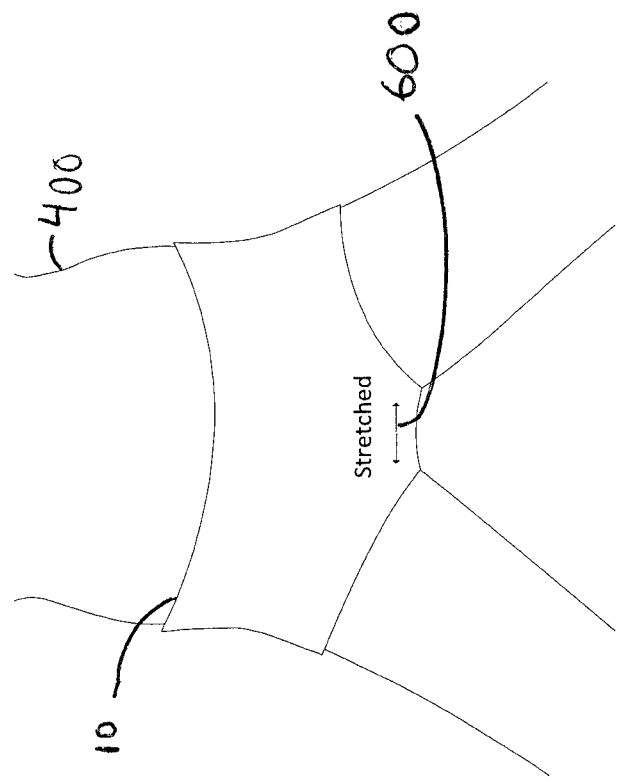
FIGS. 19A and 19B are front views showing movements of a wearer of the absorbent article, including the forces exerted upon the absorbent article as a result of such movements.
Figure 19B:
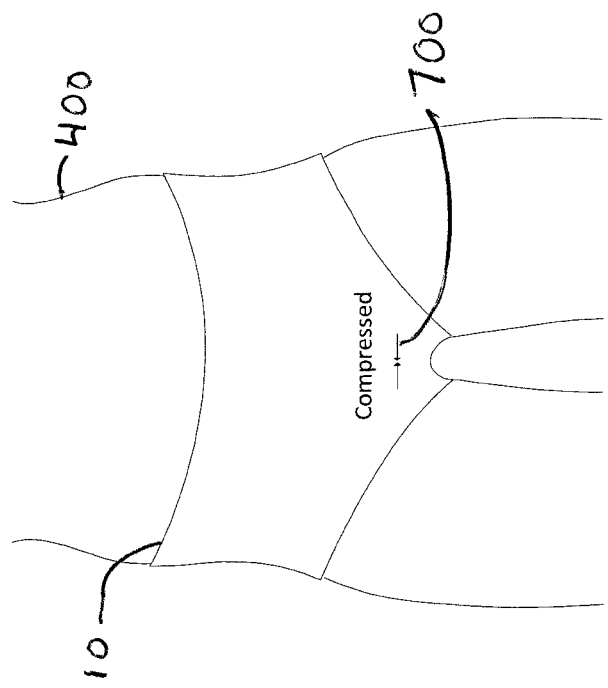

With reference to FIGS. 18A-19B, various body movements that may impart forces that affect void space 500 and absorbent core 14 are depicted. FIG. 18A depicts wearer 400 in a first position with the wearer's legs extending generally downward and generally aligned with the wearer's torso. In the first position, a stretching force 600 is imparted on a front portion of absorbent article 10, and a compression force 700 is imparted on a back portion of absorbent article 10. Such forces, resulting from movement of the wearer's body, will be imparted onto the elastics of the chassis of absorbent article 10. However, as absorbent article includes a floating absorbent core, transmission of such forces to the floating absorbent core will be reduced or eliminated in comparison to an otherwise identical absorbent article in which the absorbent core was not "floating". FIG. 18B depicts the wearer 400 in a second position with the wearer's legs extended outwards towards the front of the wearer's body, relative to the first position. In the second position, a compression force 700 is imparted onto the front portion of absorbent article 10, and a stretching force 600 is imparted on a back portion of absorbent article 10. FIG. 18C depicts the wearer 400 in a third position with the wearer's legs extended further outwards towards the front of the wearer's body, relative to the second position. In the third position, a compression force 700 is imparted onto the front portion of absorbent article 10, and a stretching force 600 is imparted on a back portion of absorbent article 10. FIG. 19A depicts wearer 400 in a fourth position, with the wearer's legs extending downwards and generally aligned with the extension of the wearer's torso. In the fourth position, a compression force 700 is imparted generally in the front crotch region of absorbent article 10. FIG. 19B depicts wearer 400 in a fifth position, with the wearer's legs spread outwards from the wearer's body relative to FIG. 19A and generally at an angle relative to the extension of the wearer's torso. In the fifth position, a stretching force 600 is imparted generally in the front crotch region of absorbent article 10.

When areas of absorbent article 10 containing floating sections of the floating absorbent core 14 are stretched, the void space 500 closes or at least shrinks in volume. When areas of absorbent article 10 containing floating sections of the floating absorbent core 14 are compressed and the elastic members 21 relax, the void space 500 opens or at least expands in volume. In some aspects, the void space 500 is never fully opened or fully closed. While being worn by a wearer, the configuration of void space 500 may fluctuate through a continuum of various configurations that reside between entirely open and entirely closed, depending on the amount of stretch and/or compression on any particular part of the floating absorbent core 14.

FIG. 20A depicts absorbent article 10 in a relaxed, compressed (i.e., contracted) state, and FIG. 20B depicts the absorbent article 10 of FIG. 20A, but in a stretched, extended state. With reference to FIGS. 20A and 20B, illustrative effects of various forces acting upon absorbent article 10 are depicted. The configuration of void space 500 may be at least partially defined or affected by the elastic state (e.g., stretched or contracted) of elastic member 21, as elastic member 21 imparts potential energy to portions of absorbent article 10, such that the void space 500 dynamically changes with the wearer's movements (i.e., more stretch leads to more tension on the elastics, which leads to a reduction in volume of the void space). In the relaxed, compressed state, void space 500 is generally in an open configuration with absorbent core 14 floating above outer chassis (here including impermeable layer 13, upper backsheet 12, and lower backsheet 11) forming void space 500. Whereas, in the stretched, extended state absorbent core 14 is positioned closer to outer chassis, such that void space 500 is generally in a closed configuration, with the volume and/or size of void space 500 reduced or eliminated. Thus, the volume of void space 500 in the stretched, extended state decreases relative to the volume of void space 500 in the relaxed, compressed state. In some aspects, the volume of void space 500 is completely eliminated in the stretched, extended state, such that void space 500 is no longer present in the stretched, extended state. Also, the width 800 of absorbent article 10 in the stretched, extended state in generally greater than that of the relaxed, compressed state, as each layer thereof is extended.

Fluid channels 200 are also modified in the stretched, extended state, relative to the relaxed, compressed state. When elastic member 21 is stretched and extended, the remainder of outer chassis is also stretched and extended. With elastic member 21 relaxed and compressed (i.e., contracted), the remainder of outer chassis becomes shirred and/or gathered, as these portions of outer chassis are attached (e.g., adhered) to elastic member 21, such that elastic forces (both compression and stretching) of elastic member 21 act upon the outer chassis. As discussed elsewhere herein, such gathering and/or shirring results, in some aspects, in the formation of peaks 201 and valleys (fluid channels 200). The stretching and extending of the outer chassis, via the stretching and extending of elastic member 21, results in the reduction in the depth of the valleys that form fluid channels 200. In some aspects, elastic member 21 and outer chassis may be stretched to a degree sufficient to eliminate such peaks 201 and valleys, such that fluid channels 200 are not present in the stretched and extended state, as shown in FIG. 20B. As the valleys flattened, the valleys impart force upon any liquid residing within fluid channels 200, causing the liquid to be directed along the fluid channels 200 to another location within absorbent article (e.g., within void space 500 or reabsorbed into absorbent core 14). Fluid channels 200 may be directed laterally, longitudinally, at an angle to both the lateral and longitudinal extent of the floating absorbent core 14, or combinations thereof. The direction of the extend of fluid channels 200 and/or of void space 500 may be designed to direct fluid flow within fluid channels 200 and/or void space 500 to a desired location.

As the upper portion of absorbent article 10 (here including topsheet 15 attached to absorbent core 14) is only partially attached (e.g., adhered) to the outer chassis of absorbent article 10, the elastic forces of elastic member 21 are not transferred to topsheet 15 and absorbent core 14, or are at least transferred to topsheet 15 and absorbent core 14 to a lesser degree than such elastic forces are transferred to the outer chassis and transferred to topsheet 15 and absorbent core 14 to a lesser degree than would be the case in an otherwise identical absorbent article in which the absorbent core 14 is not floating.

When absorbent article moves from a relatively relaxed, compressed state (FIG. 20A) to a relatively stretched, extended state (FIG. 20B) with fluid (liquid and/or gas) present within void space 500, the relative movement of absorbent core 14 towards the outer chassis, at least partially closing void space 500, imparts forces (void closing forces) onto the fluid within void space 500. In some such aspects, liquid is directed by such forces to flow within void space 500 to another location within void space 500, to absorb into absorbent core 14, or combinations thereof.

Changing of void space 500 from a relatively closed configuration to a relatively open configuration may promote ventilation and/or drying of absorbent article 10. In some such aspects, gas present within void space 500 is directed by such forces to: flow within void space 500 to another location within void space 500, absorb into absorbent core 14, ventilate to outside of absorbent article 10, or combinations thereof. When void space 500 moves from a relatively closed configuration to a relatively open configuration, such opening of void space 500 may create a vacuum force, drawing in air (e.g., from outside of absorbent article 10); thereby, promoting ventilation and/or drying of portions of absorbent article 10 (e.g., absorbent core 14).

In some aspects, absorbent article 10 cycles through the relatively stretched, extended configuration and relatively relaxed, compressed configuration as various forces are imparted on absorbent article 10, such as forces resulting from various movements of the wearer's body. In such aspects, void space 500 correspondingly cycles through the relatively closed configuration and relatively open configuration as various forces are imparted on absorbent article 10, such as forces resulting from various movements of the wearer's body. Such cycling between the open and closed configurations of void space 500 promotes continued, cyclical ventilation, fluid distribution, fluid retention, or combinations thereof throughout the time period within which the wearer wears absorbent article 10.

FIG. 21A depicts absorbent article 10 in a relaxed, compressed (i.e., contracted) state, showing the direction of the compression (contraction) force 700 thereon, and the fluid flow lines 203 indicating the direction of fluid flow within void space 500. As elastic member 21 is stretched and extended, floating absorbent core 14 is compressed towards the outer chassis of absorbent article 10, forcing fluid to flow within void space 500, such as along fluid flow lines 203. FIG. 21B depicts the absorbent article 10 of FIG. 21A, but in a stretched, extended state.

Void spaces 500 may thus be created via active elastication, either from the floating absorbent core 14 or interaction between the floating absorbent core 14 bonded (e.g., at discrete points) to the elasticated chassis 17 as various forces cause void space 500 to form (i.e., to open) and un-form (i.e., close). Such active elastication may form void spaces that repeatedly cycle between a low-volume (flattened/stressed) configuration and a higher-volume (pillowed/unstressed) configuration. Such repeated cycling of the void space 500 between open and closed configurations, or between lower- and higher-volume configurations, act as active "pumps" that push fluids along within and through void space 500; thereby, creating a bellows effect that provides for increased liquid distribution and gas ventilation. This bellows effect, created as the wearer moves around, causes void space 500 to open and close, providing ventilation or even pumping of air through and around the chassis 17 of absorbent article. Increased ventilation within void space 500 results in a lower relative humidity in the microclimate at and around the wearer's skin, which lead to lower skin hydration. Thus, increased ventilation can result in increased comfort for the wearer of the absorbent article 10. The bellows effect may direct fluid away from the bond points between the floating absorbent core 14 and the chassis 17. In aspects where the bonding zones 19 are in the center of floating absorbent core 14 (FIG. 8), the fluid will be directed towards the sides and longitudinally. With configurations having the bonding zones 19 positioned at the sides of the floating absorbent core 14, the fluid may be directed towards the center of the floating absorbent core 14, as well as longitudinally Mechanisms for the dynamic changes in the void space 500 (e.g., changes to the volume, shape, profile) include, but are not necessarily limited to loading (e.g., compression) on the absorbent article 10 due to relative position and movement of the wearer's body. Such movements cause changes to the void space 500 at least in part because the movements impart force upon the elastic members 21 of the elasticated chassis 17, resulting in stretching and tension forced being applied to the elastic members 21, which causes flattening or pillowing of the floating absorbent core 14.

Void Space—Formed Below Impermeable Layer

Figure 22:
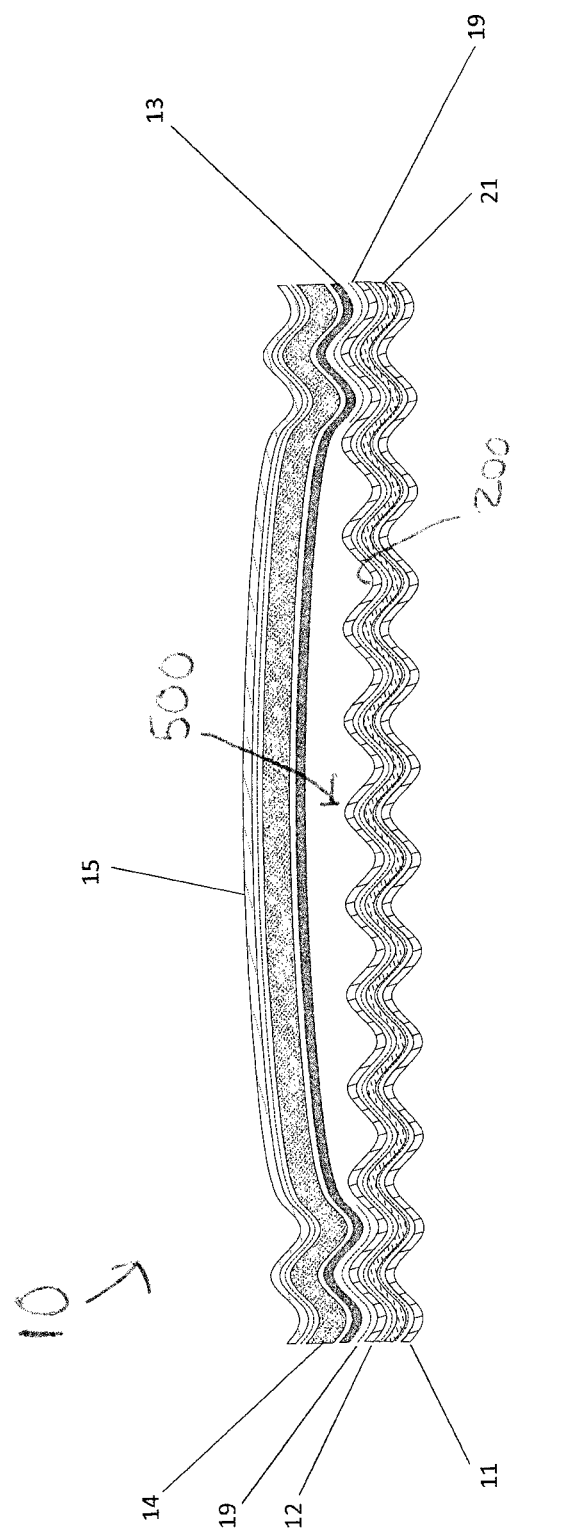
FIG. 22 is a cross-sectional view through an absorbent article, similar to the cross-sectional view through line A"-A" in FIG. 6A, but with the impermeable layer attached to the absorbent core and floating above the void space.

With reference to FIG. 22, in some aspects void space is formed below impermeable layer 13. Impermeable layer 13 may be attached (e.g., adhered or otherwise laminated thereto) to the bottom surface of floating absorbent core 14 such that impermeable layer 13 floats with floating absorbent core 14 above elasticated chassis 17, forming void space 500 therebetween. In some such aspects, impermeable layer 13 is contiguously attached to floating absorbent core 14.

The void space 500 formed below impermeable layer 13 may serve as a conduit for moist air exiting impermeable layer 13 (e.g., a breathable barrier film), facilitating in the movement of moist air out of the absorbent article 10. Such ventilation in the skin microclimate promotes drying and lowers skin hydration for better skin health. In addition, the separation between impermeable layer 13 and the outer nonwoven of the elasticated chassis (i.e., upper backsheet 12) can mitigate the damp and clammy feeling on the outer surface of the absorbent article 10 caused by vapor condensation.

Void Space—Bonding Patterns

In some aspects, the dynamic properties of the floating absorbent core 14 and associated void space 500 (i.e., the responsiveness to forces and cycling through configurations) may be modified and/or enhanced by configuring the bonding pattern between the floating absorbent core 14 and the underlying outer chassis of absorbent article 10 (i.e., by designing the spacing, placement, and/or arrangement of bonding zones 19). Such configurations of the bonding pattern between the floating absorbent core 14 and the underlying outer chassis of absorbent article 10 may be used to modify the shape, volume, relative placement within absorbent article 10, size, responsiveness to forces (elastic forces and other forces exerted by body movements), or combinations thereof of floating absorbent core 14 and void space 500.

Increased bonding (i.e., more and/or larger bonding zones 19) of absorbent core 14 to the underlying outer chassis of absorbent article 10 results in a decrease in the level of "floating" of absorbent core 14, such that absorbent core 14 is further elastically coupled to elastic member 21 (relative to less bonding). The bonding pattern of the floating absorbent core 14 to the elasticated chassis 17 will, at least in part, determine the profile of the void space 500 and the floating absorbent core 14. Bonded areas of the floating absorbent core 14 will be gathered by contraction of the elastic members 21 of the elasticated chassis 1, whereas, unbonded areas of the floating absorbent core 14 will not be gathered, or will be less gathered than the bonded areas thereof. In some aspects, increased bonding of the floating absorbent core 14 to the elasticated chassis 17 may form bonding patterns between absorbent core 14 and the underlying outer chassis of absorbent article 17 that are configured to enhance fluid retention, fluid distribution, ventilation, or combinations thereof. For example, bonding patterns between absorbent core 14 and the underlying outer chassis of absorbent article 17 may be configured to directed fluid flow within void space 500 to particular locations within absorbent article 10. Bonding patterns between absorbent core 14 and the underlying outer chassis of absorbent article 17 may be designed and/or configured to form fluid retention zones within void space 500. As such, by configuring the bonding pattern between absorbent core 14 and the underlying outer chassis of absorbent article 17, the design of absorbent article 10 may be optimized to advantageously combine the features and benefits of the floating absorbent core 14 with the features and benefits of a void space 500 defined by a particular bonding pattern (e.g., enhancements to the fluid retention and/or fluid distribution and/or ventilation properties).

Bonding patterns between absorbent core 14 and the underlying outer chassis of absorbent article 17 may be designed and/or configured to form pillows of floating absorbent core 14. As used herein, a "pillow" refers to a floating absorbent core having a void space formed thereunder that is defined by one or more bonding zones. For example, floating absorbent core 14 of FIGS. 9A and 9B is a single pillow floating core, and floating absorbent core 14 of FIG. 8 is a double pillow floating core, defining two void spaces, each defined via bonding zone 19.

In some aspects, floating absorbent core 14 provides a cushioning to the wearer of absorbent article 10, such as via the pillows. As force is exerted via the wearer's body onto topsheet 15 and absorbent core 14, topsheet 15 and absorbent core 14 are responsive to move, relatively, towards the outer chassis of absorbent article 10. The compression of the pillow structure cushions the interaction between the wearer's body and absorbent article 10. As such, floating absorbent core 14 provides improved fit and comfort to the wearer.

In some aspects, the bonding (e.g., bond lines) between the floating absorbent core 14 and the elasticated chassis 17 extend laterally, longitudinally, at an angle to both the lateral and longitudinal extend of the floating absorbent core 14, or combinations thereof. In some aspects, bond lines between the floating absorbent core 14 and the elasticated chassis 17 are linear, non-linear (e.g., curvilinear), or combinations thereof.

In some aspects, the bonding between the floating absorbent core 14 and the elasticated chassis 17 can be configured to provide a longitudinally oriented and extending void space 500. Longitudinally oriented and extending void spaces 500 allow fluid to flow longitudinally therein, allowing for fuller utilization of absorbent core 14 in comparison to cross-directionally oriented and extending void spaces, which may result in leakage of fluids along the sides of void space 500 the absorbent article 10.

In some aspects, the bonding between the floating absorbent core 14 and the elasticated chassis 17 can be configured to provide a non-linear void space. Non-linear void spaces may direct liquid to specific areas in the floating absorbent core 17, such as to the extremities (e.g., towards the waist) such that full utilization of the absorbent core 14 is accomplished.

As would be clear to one of skilled in the art, the void spaces 500 disclosed herein provide a mechanism for moving liquid and/or air within the absorbent article 10.

Void Space—Treatments and Modifications

In some aspects, one or more treatments or modifications of void space 500 may provide desired enhancements thereto. For example and without limitation, a wettable surface may be formed within void space 500, allowing for faster and better fluid movement within void space. The wettable surface may be formed on one or more of the surfaces that form the interior walls of the void space 500.

For example, in FIG. 9A, the top, or bodyside, surface of impermeable layer 13 upon which the peaks 201 and fluid channels 200 are formed may be a wettable surface. In such configurations having the void space 500 formed between floating absorbent core 14 and the impermeable layer 13 (e.g., polyethylene barrier film), fluid distribution properties may be enhanced by modifying impermeable layer 13 to be wettable. In some such aspects, all or at least a part of the inner surface area of impermeable layer 13 that defines a portion of the interior wall of void space 500 may be modified to be wettable. One skilled in the art understands that various techniques may be used to impart wettable characteristics onto a material including, but not limited to, the addition of a surfactant to the surface, as well as corona or plasma treatment of the surface. For microporous films, such as filled PE film, treatment conditions may be optimized to minimize any reduction in liquid barrier properties. In some aspects, impermeable layer 13 is formed of a material (e.g., a monolithic barrier film) that is inherently breathable and wettable. For example, certain grades of polyethylene block amide polymers (PEBA) function as breathable liquid barriers that are wettable, and can be substituted for microporous polyethylene (PE) films. Use of such a wettable impermeable layer 13 within void space 500 provides additional fluid distribution properties thereto.

Method of Making an Absorbent Article

Absorbent article 10 may be made by methods well known to those of ordinary skill in the art, such as those disclosed in U.S. Pat. Nos. 7,462,172, 7,361,246, and 8,148, 59; and U.S. Pat. Appl. Publ. Nos. US 2012/0071852, US 2014/0303582 A1, and US 2014/0276508, which are each incorporated herein in their entirety.

In some aspects, a method of making the absorbent article disclosed herein includes attaching (e.g., adhering) an absorbent core to an elasticated chassis via one or more discrete bonding zones such that at least a portion of the absorbent core is floating above the underlying elasticated chassis with a void space located therebetween. The method may include configuring (size, shape, placement) the discrete bonding zones to provide a void space having the desired shape, size, volume, profile, and fluid distribution, retention, and ventilation properties, as described above. The method may include elasticizing the chassis of the absorbent article, and at least partially isolating the floating absorbent core from the elasticated chassis. In some aspects, the method includes forming a three-piece diaper absorbent article.

The method may include designing the configuration of the void space and/or floating absorbent core such that the configurations of the void space and/or floating absorbent core are responsive to movements by a wearer of the absorbent article. In some such aspects, the void space and/or floating absorbent core are designed and/or configured such that the void space cycles through open and closed configurations, or low-volume and higher-volume configurations.

The absorbent article formed via this method may be any of the absorbent articles disclosed herein, and may have any or all of the structural and/or functional properties described herein, including, but not limited to, the structural and/or functional properties of the absorbent articles depicted in any of FIGS. 1A-22.

Although the present embodiments and advantages have been described in detail, it should be understood that various changes, substitutions and alterations can be made herein without departing from the spirit and scope as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An absorbent article comprising:
an absorbent core composite including an absorbent core and an elasticated chassis, wherein the absorbent core is bonded to the elasticated chassis via at least one discrete bonding zone that bonds the absorbent core with the elasticated chassis and imparts elasticity thereto, and wherein the absorbent core includes at least one unbonded zone that is unbonded with the elasticated chassis, wherein said bonded zone comprises surface area of a bottom surface of the absorbent core that is bonded with the elasticated chassis, and wherein said unbonded zone comprises surface area of the bottom surface of the absorbent core that is unbonded with the elasticated chassis, wherein multiple void spaces are formed between the absorbent core and the elasticated chassis.

2. The absorbent article of claim 1, wherein said unbonded surface area of the absorbent core is unrestrained by the elasticated chassis and is movable relative to the elasticated chassis.

3. The absorbent article of claim 1, wherein said unbonded surface area of the absorbent core has an unbonded free width that ranges from 50% to 95% of the width of the absorbent core for a core length of up to 50% of the total length of the core.

4. The absorbent article of claim 1, wherein said unbonded surface area of the absorbent core has an unbonded free area that is equal to greater than 50% of the total surface area of the bottom surface of the core.

5. The absorbent article of claim 1, wherein said unbonded surface area of the absorbent core has an unbonded free width that ranges from 70% to 95% of the total width of the absorbent core for a core length ranging from 60% to 95% of the total length of the core.

6. The absorbent article of claim 1, wherein the elasticated chassis includes and a plurality of laterally extended elastics.

7. The absorbent article of claim 6, wherein the bonding zones couple the absorbent core to the elasticated chassis at regions of the elasticated chassis that do not include the plurality of extended elastics.

8. The absorbent article of claim 1, wherein the absorbent core includes one or more elastic members incorporated therein.

9. The absorbent article of claim 8, wherein the elastic members of the absorbent core are isolated from elastic members of the elasticated chassis.

10. The absorbent article of claim 1, wherein an underside of the absorbent core includes an embossed pattern that forms channels between absorbent core and the elasticated chassis.

11. The absorbent article of claim 1, wherein, when elastics of the elasticated chassis are in a contracted state, a void space of the multiple void spaces is positioned between the absorbent core and the elasticated chassis, wherein the void space of the multiple void spaces is coincident with the unbonded zones of the absorbent core.

12. The absorbent article of claim 11, wherein, when elastics of the elasticated chassis are in the contracted state, the elasticated chassis is gathered or shirred such that peaks and valleys are formed in the elasticated chassis, wherein the valleys form fluid channels within the void space of the multiple void spaces.

13. The absorbent article of claim 11, wherein the void space of the multiple void spaces includes at least one fluid retention zone.

14. The absorbent article of claim 11, wherein the void space of the multiple void spaces exhibits dynamic properties including a dynamic volume, a dynamic shape, dynamic fluid distribution properties, dynamic fluid retention properties, dynamic ventilation and drying properties, or combinations thereof, wherein the dynamic properties dynamically vary in response to stretching and contraction of the elastic members of the elasticated chassis.

15. The absorbent article of claim 11, wherein a bonding pattern of the bonding zones at least in partially defines the profile of the void space of the multiple void spaces and the absorbent core.

16. The absorbent article of claim 1, wherein at least some of the multiple void spaces are in direct fluid communication with other of the multiple void spaces.

17. The absorbent article of claim 1, wherein each of the multiple void spaces are fluidically isolated from the other of the multiple void spaces.

18. The absorbent article of claim 1, wherein said bonded zone comprises from 5% to 40% of the surface area of the bottom surface of the absorbent core that is bonded with the elasticated chassis, and wherein said unbonded zone comprises from 60% to 95% of the surface area of the bottom surface of the absorbent core that is unbonded with the elasticated chassis.

19. An absorbent article comprising:
an absorbent core; and
an elasticated chassis imparting elasticity to the absorbent core at one or more bonding zones; and
multiple void spaces formed between the elasticated chassis and the absorbent core, the multiple void spaces coincident with unbonded zones of the absorbent core where the absorbent core is unbonded to the elasticated chassis.

20. A method of making an absorbent article comprising:
bonding an absorbent core to an elasticated chassis at one or more discrete boding zones, such that the absorbent core is unbonded from the elasticated chassis at one or more unbonded zones;
wherein a surface area of a bottom surface of the absorbent core is bonded with the elasticated chassis, and wherein a surface area of the bottom surface of the absorbent core is unbonded with the elasticated chassis; and
wherein multiple void spaces are formed between the absorbent core and the elasticated chassis.

21. The method of claim 20, wherein from 5% to 40% of the surface area of the bottom surface of the absorbent core is bonded with the elasticated chassis, and wherein from 60% to 95% of the surface area of the bottom surface of the absorbent core is unbonded with the elasticated chassis.

* * * * *